(12) United States Patent
Ahmed et al.

(10) Patent No.: US 10,357,469 B2
(45) Date of Patent: Jul. 23, 2019

(54) DIAGNOSTIC ASSAY AND TREATMENT FOR PREECLAMPSIA

(71) Applicant: Aston University, West Midlands (GB)

(72) Inventors: Asif Ahmed, West Midlands (GB); Keqing Wang, West Midlands (GB); Shakil Ahmad, Birmingham (GB)

(73) Assignee: ASTON UNIVERSITY, Birmingham, West Midlands (GB)

( * ) Notice: Subject to any disclaimer, the term of this patent is extended or adjusted under 35 U.S.C. 154(b) by 0 days.

(21) Appl. No.: 15/551,468

(22) PCT Filed: Feb. 18, 2016

(86) PCT No.: PCT/GB2016/050408
§ 371 (c)(1),
(2) Date: Aug. 16, 2017

(87) PCT Pub. No.: WO2016/132136
PCT Pub. Date: Aug. 25, 2016

(65) Prior Publication Data
US 2018/0036271 A1 Feb. 8, 2018

(30) Foreign Application Priority Data

Feb. 18, 2015 (GB) .................................. 1502741.0
Feb. 27, 2015 (GB) .................................. 1503316.0
Mar. 17, 2015 (GB) .................................. 1504466.2

(51) Int. Cl.
G01N 33/68 (2006.01)
A61K 31/198 (2006.01)

(52) U.S. Cl.
CPC ......... *A61K 31/198* (2013.01); *G01N 33/689* (2013.01); *G01N 2800/368* (2013.01)

(58) Field of Classification Search
None
See application file for complete search history.

(56) References Cited

U.S. PATENT DOCUMENTS

| 8,361,514 | B2 | 1/2013 | Gojon-Romanillos | |
|---|---|---|---|---|
| 2001/0056068 | A1* | 12/2001 | Chwalisz | A61K 31/195 514/310 |
| 2012/0040371 | A1 | 2/2012 | Buhimschi | |
| 2016/0012902 | A1 | 5/2016 | Ahmed et al. | |

FOREIGN PATENT DOCUMENTS

| JP | 2006151861 | 6/2006 |
|---|---|---|
| WO | 2004/073623 | 9/2004 |
| WO | 2011161436 | 12/2011 |
| WO | 2016/132136 | 8/2016 |

OTHER PUBLICATIONS

Dorniak-Wall et al., Journal of Human Hypertension (2014), 28(4), pp. 230-235.*
Lowe, Journal of Human Hypertension (2014), 28(4), p. 282.*
Vaughan et al., Hypertension in Pregnancy (2002), 21(3), pp. 205-223.*
Kumasawa, Keiichi, et al., "Prevastatin induces placental growth factor (PGF) and ameliorates preeclampsia in a mouse model." Proceedings of the National Academy of Sciences (2011), 108(4), pp. 1197-1198.*
PCT Search Report prepared for PCT/GB2016/050408, dated Jul. 15, 2016.
Delić, Ratko, et al. "Statistical regression model of standard and new laboratory markers and its usefulness in prediction of preeclampsia." The Journal of Maternal-Fetal & Neonatal Medicine 27.4 (2014): 388-392.
Sankaralingam, Sowndramalingam, Han Xu, and Sandra T. Davidge. "Arginase contributes to endothelial cell oxidative stress in response to plasma from women with preeclampsia." Cardiovascular research 85.1 (2009): 194-203.
George, Eric M., et al. "Heme oxygenase-1 attenuates hypoxia-induced sFlt-1 and oxidative stress in placental villi through its metabolic products CO and bilirubin." International journal of hypertension 2012 (2011).
Molvarec, Attila, et al. "Circulating angiogenic factors determined by electrochemiluminescence immunoassay in relation to the clinical features and laboratory parameters in women with pre-eclampsia." Hypertension Research 33.9 (2010): 892-898.
Zhao W, Zhang J, Lu Y, Wang R. The vasorelaxant effect of H(2)S as a novel endogenous gaseous K(ATP) channel opener. Embo J. 2001;20(21):6008-6016.
Papapetropoulos A, Pyriochou A, Altaany Z, Yang G, Marazioti A, Zhou Z, Jeschke MG, Branski LK, Herndon DN, Wang R, Szabo C. Hydrogen sulfide is an endogenous stimulator of angiogenesis. Proc Natl Acad Sci U S A. 2009;106(51):21972-21977.
Zanardo RC, Brancaleone V, Distrutti E, Fiorucci S, Cirino G, Wallace JL. Hydrogen sulfide is an endogenous modulator of leukocyte-mediated inflammation. Faseb J. 2006;20(12):2118-2120.
Blackstone E, Roth MB. Suspended animation-like state protects mice from lethal hypoxia. Shock. 2007;27(4):370-372.
Elrod JW, Calvert JW, Morrison J, Doeller JE, Kraus DW, Tao L, Jiao X, Scalia R, Kiss L, Szabo C, Kimura H, Chow CW, Lefer DJ. Hydrogen sulfide attenuates myocardial ischemia-reperfusion injury by preservation of mitochondrial function. Proc Natl Acad Sci U S A. 2007;104(39):15560-15565.

(Continued)

*Primary Examiner* — Brian J Davis
(74) *Attorney, Agent, or Firm* — Brannon, Sowers & Cracraft PC

(57) ABSTRACT

Described is a method of diagnosis or prognosis of preeclampsia in a pregnant subject, comprising providing a sample from a pregnant subject and measuring the ratio between the amount of (a) one or both of sFlt-1 and PlGF, and (b) one or both of a breakdown product of heme and a breakdown product of arginine, in the sample. Also described are assay kits and a computer adapted for use in the method. Also described is a method of treating preeclampsia, comprising administering a pharmaceutically effective amount of L-arginine and/or citrulline and an inhibitor of arginase or pharmaceutically acceptable salts thereof. Also described is a method of treating cancer, comprising treating a subject with a therapeutically effective amount of an anti-VEGF compound, L-arginine and an arginase inhibitor.

8 Claims, 21 Drawing Sheets

(56) References Cited

OTHER PUBLICATIONS

Kabil O, Vitvitsky V, Xie P, Banerjee R. The quantitative significance of the transsulfuration enzymes for H2S production in murine tissues. Antioxid Redox Signal. 2011;15(2):363-372.
Ramma W, Buhimschi IA, Zhao G, Dulay AT, Nayeri UA, Buhimschi CS, Ahmed A. The elevation in circulating anti-angiogenic factors is independent of markers of neutrophil activation in preeclampsia. Angiogenesis. 2012;15 (3):333-340.
Lee M, J. Effects of Hydrogen Sulfide-releasing L-DOPA Derivatives on Glial Activation. Biol Chem (2010) 285, 17318-17328.
Ahmad S, Ahmed A. Elevated placental soluble vascular endothelial growth factor receptor-1 inhibits angiogenesis in preeclampsia. Circ Res. 2004;95(9):884-891.
Predmore B.L. et al.Hydrogen Sulfide in Biochemistry and Medicine (Antioxidants and Redox Signalling (2012) 17 (1) 119-140).
Banerjee R. Hydrogen sulfide: redox metabolism and signaling. Antioxid Redox Signal. 2011;15(2):339-341.
Hogberg U. The World Health Report 2005: "make every mother and child count" -including Africans. Scand J Public Health. 2005;33(6):409-411.
Bannenberg G.L. and Viera HLA. Therapeutic applications of the gaseous mediators carbon monoxide and hydrogen sulfide. (Expert Opin. Ther. Patents (2009) 19(5) 663-682).
Thadhani R, Mutter WP, Wolf M, Levine RJ, Taylor RN, Sukhatme VP, Ecker J, Karumanchi SA. First trimester placental growth factor and soluble fms-like tyrosine kinase 1 and risk for preeclampsia. J Clin Endocrinol Metab. 2004;89(2):770-775.
Egbor M, Ansari T, Morris N, Green CJ, Sibbons PD. Morphometric placental villous and vascular abnormalities in early- and late-onset pre-eclampsia with and without fetal growth restriction. Bjog. 2006;113(5):580-589.
Ahmed A, Cudmore MJ. Can the biology of VEGF and haem oxygenases help solve pre-eclampsia? Biochem Soc Trans. 2009;37(Pt 6):1237-1242.
Maynard SE, Karumanchi SA. Angiogenic factors and preeclampsia. Semin Nephrol. 2011;31(1):33-46.
Levine RJ, Maynard SE, Qian C, Lim KH, England LJ, Yu KF, Schisterman EF, Thadhani R, Sachs BP, Epstein FH, Sibai BM, Sukhatme VP, Karumanchi SA. Circulating angiogenic factors and the risk of preeclampsia. N Engl J Med. 2004;350(7):672-683.
Levine RJ, Lam C, Qian C, Yu KF, Maynard SE, Sachs BP, Sibai BM, Epstein FH, Romero R, Thadhani R, Karumanchi SA. Soluble endoglin and other circulating antiangiogenic factors in preeclampsia. N Engl J Med. 2006;355(10):992-1005.
Chen CP. Placental abnormalities and preeclampsia in trisomy 13 pregnancies. Taiwan J Obstet Gynecol. 2009;48(1):3-8.
Ramma W, Ahmed A. Is inflammation the cause of pre-eclampsia? Biochem Soc Trans. 2011;39(6):1619-1627.
Saxena AR, Karumanchi SA, Brown NJ, Royle CM, McElrath TF, Seely EW. Increased sensitivity to angiotensin II is present postpartum in women with a history of hypertensive pregnancy. Hypertension. 2010;55(5):1239-1245.
Damsky CH, Fitzgerald ML, Fisher SJ. Distribution patterns of extracellular matrix components and adhesion receptors are intricately modulated during first trimester cytotrophoblast differentiation along the invasive pathway, in vivo. J Clin Invest. 1992;89(1):210-222.
Savvidou MD, Nood M, Anderson JM, Hingorani AD, Nicolaides KH. Maternal endothelial function and serum concentrations of placental growth factor and soluble endoglin in women with abnormal placentation. Obstet Gynecol. 2008;32(7):871-876.
Foidart JM, Munaut C, Chantraine F, Akolekar R, Nicolaides KH. Maternal plasma soluble endoglin at 11-13 weeks' gestation in pre-eclampsia. Ultrasound Obstet Gynecol. 2010;35(6):680-687.
Cudmore M, Ahmad S, Al-Ani B, Fujisawa T, Coxall H, Chudasama K, Devey LR, Wigmore SJ, Abbas A, Hewett PW, Ahmed A. Negative regulation of soluble Flt-1 and soluble endoglin release by heme oxygenase-1. Circulation. 2007;115(13):1789-1797.

Cross JC, Simmons DG, Watson ED. Chorioallantoic morphogenesis and formation of the placental villous tree. Ann NY Acad Sci. 2003;995:84-93.
You XJ, Xu C, Lu JQ, Zhu XY, Gao L, Cui XR, Li Y, Gu H, Ni X. Expression of cystathionine beta-synthase and cystathionine gamma-lyase in human pregnant myometrium and their roles in the control of uterine contractility. PLoS ONE. 2011;6(8):e23788.
Ahmad, Shakil, et al. "Direct evidence for endothelial vascular endothelial growth factor receptor-1 function in nitric oxide—mediated angiogenesis." Circulation research 99.7 (2006): 715-722.
Levine RJ, Thadhani R, Qian C, Lam C, Lim KH, Yu KF, Blink AL, Sachs BP, Epstein FH, Sibai BM, Sukhatme VP, Karumanchi SA. Urinary placental growth factor and risk of preeclampsia. Jama. 2005;293(1):77-85.
Noori M, Donald AE, Angelakopoulou A, Hingorani AD, Williams DJ. Prospective study of placental angiogenic factors and maternal vascular function before and after preeclampsia and gestational hypertension. Circulation. 2010;122(5):478-487.
James, P. R., & Nelson-Piercy, C. (2004). Management of hypertension before, during, and after pregnancy. Heart, 90(12), 1499-1504.
Torry DS, Wang HS, Wang TH, Caudle MR, Torry RJ. Preeclampsia is associated with reduced serum levels of placenta growth factor Am J Obstet Gynecol. 1998;179(6 Pt 1):1539-1544.
Taylor RN, Grimwood J, Taylor RS, McMaster MT, Fisher SJ, North RA. Longitudinal serum concentrations of placental growth factor: evidence for abnormal placental angiogenesis in pathologic pregnancies. Am J Obstet Gynecol. 2003;188(1):177-182.
Buhimschi CS, Norwitz ER, Funai E, Richman S, Gutter S, Lockwood CJ, Buhimschi IA. Urinary angiogenic factors cluster hypertensive disorders and identify women with severe preeclampsia. Am J Obstet Gynecol. 2005;192(3):734-741.
Rossoni, G., Manfredi, B., Tazzari, V., Sparatore, A., Trivulzio, S., Del Soldato, P., & Berti, F. (2010). Activity of a new hydrogen sulfide-releasing aspirin (ACS14) on pathological cardiovascular alterations induced by glutathione depletion in rats. European journal of pharmacology, 648(1), 139-145.
Tao, Xia, (2005). 1, Ding Ya-guang 2, Zhang Xiao-xiao 1, Li Xiao-hui 2, Zhang Chun-yu 2, Jin Hong-fang 2, Du Jun-bao# 2, Tang Chao-shu 3.(Department of Obstetric and Gynecology, First Hospital, Peking University, Beijing 100034, China); Changes in a new gaseous signal molecule, hydrogen sulfide (H _ (2S)), in patients with pregnancyinduced hypertension syndrome [J]. Chinese Journal of Medicine, 1.
Hodges, Jennifer, et al. "765: Human placental expression of the hydrogen sulfide synthesizing system: effects of gestational age and preeclampsia." American Journal of Obstetrics & Gynecology 206.1 (2012): S338.
Patel, Pushpa, et al. "The endogenous production of hydrogen sulphide in intrauterine tissues." Reproductive Biology and Endocrinology 7.1 (2009): 10.
Pan, Ji-gang, et al. "Effects of hydrogen sulphide on the proliferation and apoptosis of human fetal lung fibroblasts during hypoxia [J]." Chinese Pharmacological Bulletin 3 (2010): 008.
Robinson et al. (2012) A new slow releasing, H2S generating compound, GYY4137 relaxes spontaneous and oxytocin stimulated contractions of human and rat pregnant myometrium. PLOS One, vol. 7, No. 9, p. e46278.
Holwerda, Kim M., et al. "Gasotransmitters." Hypertension 62.4 (2013): 653-659.
Holwerda, K. M., et al. "Hydrogen sulfide producing enzymes in pregnancy and preeclampsia." Placenta 33.6 (2012): 518-521.
Yu et al. (2012) Effects of SAC on oxidative stress and NO availability in placenta: potential benefits to preeclampsia. Placenta, vol. 33, No. 6, pp. 487-494.
Cindrova-Davies et al. (2013) Reduced cystathionine ã-lyase and increased mirR-21 expression are associated with increased vascular resistance in growth-restricted pregnancies. The American Journal of Pathology, vol. 182, No. 4, pp. 1448-1458.
Elrod JW, Calved JW, Morrison J, Doeller JE, Kraus DW, Tao L, Jiao X, Scalia R, Kiss L, Szabo C, Kimura H, Chow CW, Lefer DJ. Hydrogen sulfide attenuates myocardial ischemia-reperfusion injury by preservation of mitochondrial function. *Proc Natl Acad Sci U S A*. 2007;104(39):15560-15565.

(56) References Cited

OTHER PUBLICATIONS

Savvidou MD, Noon M, Anderson JM, Hingorani AD, Nicolaides KH. Maternal endothelial function and serum concentrations of placental growth factor and soluble endoglin in women with abnormal placentation. *Ultrasound Obstet Gynecol.* 2008;32(7):871-876.
Folded JM, Munaut C, Chantraine F, Akolekar R, Nicolaides KH. Maternal plasma soluble endoglin at 11-13 weeks' gestation in pre-eclampsia. *Ultrasound Obstet Gynecol.* 2010;35(6):680-687.
Olson, Kenneth R. "The therapeutic potential of hydrogen sulfide: separating hype from hope." *American Journal of Physiology-Regulatory, Integrative and Comparative Physiology* 301.2 (2011): R297-R312.
Robinson, Hayley, and Susan Wray. "A new slow releasing, H2S generating compound, GYY4137 relaxes spontaneous and oxytocin-stimulated contractions of human and rat pregnant myometrium." *PloS one* 7.9 (2012): e46278.
Yu, J., et al. "Effects of SAC on oxidative stress and NO availability in placenta: potential benefits to preeclampsia." *Placenta* 33.6 (2012): 487-494.
Cindrova-Davies, Tereza, et al. "Reduced cystathionine γ-lyase and increased miR-21 expression are associated with increased vascular resistance in growth-restricted pregnancies: hydrogen sulfide as a placental vasodilator." *The American journal of pathology* 182.4 (2013): 1448-1458.
Holwerda, Kim M., et al. "Gasotransmitters: a solution for the therapeutic dilemma in preeclampsia?." *Hypertension* 62.4 (2013): 653-659.
PCT Search Report prepared for PCT/GB2014/050408, dated May 21, 2014.
Delic, Ralko, et al. "Statistical regression model of standard and new laboratory markers and its usefulness in prediction of preeclampsia." *The Journal of Maternal-Fetal & Neonatal Medicine* 27.4 (2014): abstract.
Sankaralingam, Sowndramalingam, Han Xu, and Sandra T. Davidge. "Arginase contributes to endothelial cell oxidative, tress in response to plasma from women with preeclampsia." *Cardiovascular research* 85.1 (2009): 194-203.
George, Eric M., et al. "Heme oxygenase-1 attenuates hypoxia-induced sFlt-1 and oxidative stress in placental villi through its metabolic products CO and bilirubin." *International journal of hypertension* 2012 (2011 ).
Molvarec, Attila, et al. "Circulating angiogenic factors determined by electrochemiluminescence immunoassay in 5 relation to the clinical features and laboratory parameters in women with pre-eclampsia." Hypertension Research 33.9 2010): 892-898.
Noon M, Donald AE, Angelakopoulou A, Hingorani AD, Williams DJ. Prospective study of placental angiogenic factors and maternal vascular function before and after preeclampsia and gestational hypertension. *Circulation.* 2010;122(5):478-487.
Buhimschi CS, Norwitz ER, Funai E, Richman S, Guller S, Lockwood CJ, Buhimschi IA. Urinary angiogenic factors cluster hypertensive disorders and identify women with severe preeclampsia. *Am J Obstet Gynecol.* 2005;192(3):734-741.
Rossoni, Giuseppe, et al. "Activity of a new hydrogen sulfide-releasing aspirin (ACS14) on pathological cardiovascular alterations induced by glutathione depletion in rats." European journal of pharmacology 648.1-3 (2010): 139-145.

Tao Xia, "1, Ding Ya-guang 2, Zhang Xiao-xiao 1, Li Xiao-hui 2, Zhang Chun-yu 2, Jin Hong-fang 2, Du Jun-bao# 2, Tang Chao-shu 3.(Department of Obstetric and Gynecology, First Hospital, Peking University, Beijing 100034, China); Changes in a new gaseous signal molecule, hydrogen sulfide (H _ (2S)), in patients with pregnancyinduced hypertension syndrome [J]." Chinese Journal of Medicine 1 (2005).
Pei, Yanxi, et al. "Hydrogen sulfide mediates the anti-survival effect of sulforaphane on human prostate cancer cells." Toxicology and applied pharmacology 257.3 (2011): 420-428.
Ahmed, Asif. "PL15 Can Hydrogen sulfide prevent preeclampsia and fetal growth restriction?." Nitric Oxide 31 (2013): S17.
Wang, Keqing, et al. "Dysregulation of hydrogen sulfide (H2S) producing enzyme cystathionine γ-lyase (CSE) contributes to maternal hypertension and placental abnormalities in preeclampsia." Circulation (2013): Circulationaha-113.
Carson, Ray J., and Justin C. Konje. "Role of hydrogen sulfide in the female reproductive tract." Expert Review of Obstetrics & Gynecology 5.2 (2010): 203-213.
Pei et al. (2011) Hydrogen sulfide mediates the anti-survival effect of sulforaphane on human prostate cancer cells. Toxicology and applied pharmacology, vol. 257, No. 3, pp. 420-428.
Tao et al. (2005) Changes in a new gaseous signalling molecule, hydrogen sulfide, in patients with pregnancy-induced hypertension syndrome. Zhongguo Yikan, vol. 40, No. 1, pp. 39-41.
Olson et al. (2011) The therapeutic potential of hydrogen sulfide: separating hype from hope. American Journal of Physiology: Regulatory, Integrative and Comparative physiology, vol. 301, No. 2, pp. R297-R312.
Ahmed et al. (2013) Can hydrogen sulfide prevent preeclampsia and fetal growth restriction? Nitric Oxide, vol. 31, p. S17.
Wang et al. (2013) Dysregulation of hydrogen sulfide producing enzyme cystathionine-lyase contributes to maternal hypertension and placental abnormalities in preeclampsia. Circulation, vol. 127, No. 25, pp. 2514-2522.
Carson et al. (2010) Role of hydrogen sulfide in the female reproductive tract. Expert Reviews of Obstetrics & Gynecology, vol. 5, No. 2, pp. 203-213.
Agrawal, International Journal of Medicine and Public Health | Oct.-Dec. 2014 | vol. 4 | Issue 4:.350-353.
Conde-Agudelo, Agustin, et al. "Supplementation with vitamins C and E during pregnancy for the prevention of preeclampsia and other adverse maternal and perinatal outcomes: a systematic review and metaanalysis." *American Journal of Obstetrics & Gynecology* 204.6 (2011): 503-e1.
Communication Pursuant to Article 94(3) EPC for EP 14709393.4, dated Mar. 29, 2018.
Lely, State of the Art Lectures, Plenary Presentations and Oral Communications/ Pregnancy Hypertension 1, Supplement 1 (2010) S1-S41.
Marcoux, American Journal of Epidemiology, 1989, vol. 130, No. 5, 950-957.
Karumanchi, Hypertension. May 2010 ; 55(5): 1100-1101.
Dogra, Vikram S. "Imaging in Intrautering Growth Retardation." Medscape, Drugs & Diseases, Nov. 12, 2015, (6 pages).
Constantine, Maged M., and Kirsten Cleary. "Pravastatin for the prevention of preeclampsia in high-risk pregnant women." *Obstetrics and gynecology* 121.2 0 1 (2013).

\* cited by examiner

Prior Art

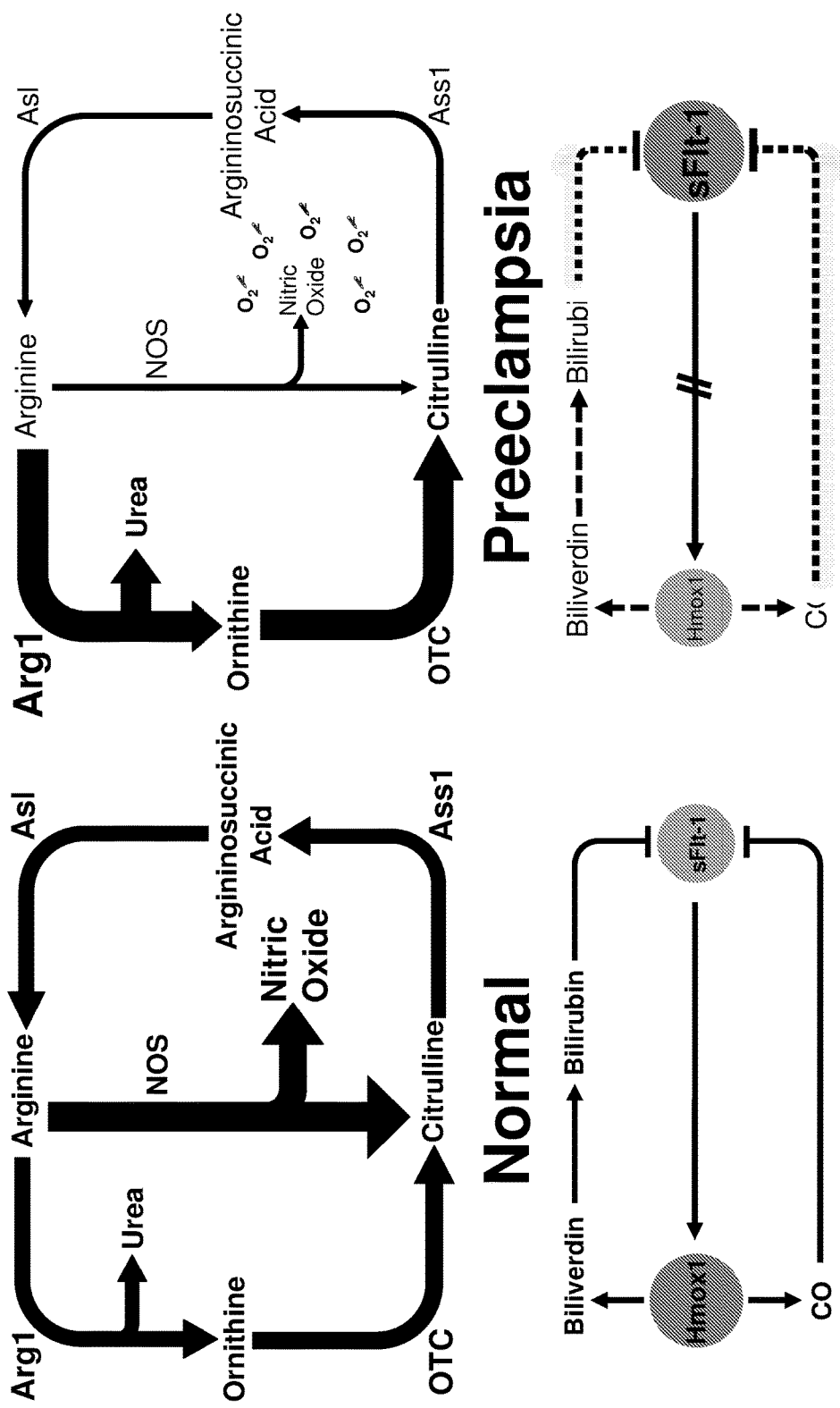
Figure 10 - Proposed schematic pathway to explain a tailored therapeutic approach to preeclampsia

DIAGNOSTIC ASSAY AND TREATMENT FOR PREECLAMPSIA

CROSS-REFERENCE TO RELATED APPLICATION

This application is a U.S. national entry application under 37 C.F.R. § 371(b) of International Application Serial No. PCT/GB2016/050408 filed Feb. 18, 2016, which claims the right of priority and benefit under 35 U.S.C. §§ 119 & 365 of GB Patent Application No. 1502741.0 filed on Feb. 18, 2015, GB Patent Application No. 1503316.0 filed on Feb. 27, 2015, and GB Patent Application No. 1504466.2 filed on Mar. 17, 2015 the disclosures of which are incorporated herein by reference in their entirety.

The invention provides methods of treating preeclampsia by delineating key underlying pathophysiological pathways and methods of diagnosis and prognosis of the preeclampsia (PE) by measuring the ratio between vascular endothelial growth factor receptor 1 (VEGFR1), also known as soluble fms-like tyrosine kinase 1 (sFlt-1)/placental growth factor (PlGF) and breakdown products of heme and arginine in a sample from a pregnant subject. This is the first invention to offer a tailored therapeutic approach to preeclampsia. Methods of reducing side effects of anti-VEGF compounds in the treatment of conditions associated with increased angiogenesis, such as cancer are also provided.

Preeclampsia is a hypertensive syndrome that affects 4-7% of all pregnancies and is a major contributor to maternal and fetal morbidity and mortality worldwide (Hogberg U. The World Health Report 2005: *Scand J Public Health*. 2005; 33(6):409-411). One in twenty pregnancies are affected by preeclampsia and the severe form (<34 weeks gestation) affecting 3 in 1000 pregnant women (Lisonkova, S., Sabr, Y., Mayer, C., Young, C., Skoll, A., and Joseph, K. S. Obstet Gynecol 2014; 124: 771-781) is on the rise in the United States (Ananth, C. V., Keyes, K. M., and Wapner, R. J. BMJ 2013; 347: f6564). Preeclampsia accounts for up to one third of all premature deliveries (Ghulmiyyah, L., and Sibai, B. *Semin Perinatol*. 2012; 36:56-59) Maternal hypertension and renal dysfunction are the hallmarks of preeclampsia (Moran P, Lindheimer M D, Davison J M. *Semin Nephrol*. 2004; 24(6):588-595). Except for the premature delivery of the baby, which can cause fetal death or severe disability, there is no therapy (Ghulmiyyah, L., and Sibai, B. *Semin Perinatol*. 2012; 36(1):56-59). It is classified as proteinuric and non-proteinuric preeclampsia (Homer C S, Brown M A, Mangos G, Davis G K. *J Hypertens*. 2008; 26(2):295-302). While women with proteinuric preeclampsia exhibit the classic symptoms such as hypertension and proteinuria after 20 weeks gestation, women with non-proteinuric preeclampsia are more likely to suffer from hypertension and liver disease. Compare with gestational hypertension, these group of women are more likely to have intrauterine growth restriction (IUGR) (Homer C S, Brown M A, Mangos G, Davis G K. *J Hypertens*. 2008; 26(2):295-302).

The exact aetiology of preeclampsia is unknown. The disruption of endothelial homeostasis (Rodgers G M, Taylor R N, Roberts J M. *Am J Obstet Gynecol*. 1988; 159(4):908-914) due to dysregulation of cytoprotective pathways [Ahmed, 2000 #4520] and imbalance of angiogenic factors (Ahmad S, Ahmed A. *Placenta*. 2001; 22(8-9):A.7; Maynard S E, Min J Y, Merchan J, Lim K H, Li J, Mondal S, Libermann T A, Morgan J P, Sellke F W, Stillman I E, Epstein F H, Sukhatme V P, Karumanchi S A. *J Clin Invest*. 2003; 111(5):649-658; Ahmad S, Ahmed A. *Circ Res*. 2004; 95(9):884-891) are increasingly recognised as key features of preeclampsia (Goulopoulou S, Davidge S T. *Trends Mol Med*. 2015; 21(2):88-97). Maternal hypertension, kidney injury and adverse pregnancy outcomes may be due to loss of VEGF activity as a result of high sFlt-1, the natural antagonist of VEGF.

VEGF receptor-1 is also known as fms-like tyrosine kinase receptor (Flt-1) and sFlt-1 is a soluble splice variant of the Flt-1 receptor, which lacks the transmembrane and cytoplasmic domains. sFlt-1 binds to VEGF with high affinity but does not stimulate mitogenesis in endothelial cells.

Importantly, circulating levels of sFlt-1, the endogenous inhibitor of VEGF as well as soluble endoglin (sEng), the cleaved product of the transforming growth factor β1 (TGF-β1) co-receptor Endoglin, are elevated several weeks prior to the onset of the clinical manifestations of preeclampsia, (Levine R J, Maynard S E, Qian C, Lim K H, England L J, Yu K F, Schisterman E F, Thadhani R, Sachs B P, Epstein F H, Sibai B M, Sukhatme V P, Karumanchi S A. *N Engl J Med*. 2004; 350(7):672-683) (Levine R J, Lam C, Qian C, Yu K F, Maynard S E, Sachs B P, Sibai B M, Epstein F H, Romero R, Thadhani R, Karumanchi S A. *N Engl J Med*. 2006; 355(10):992-1005). High maternal sFlt-1 elicits severe preeclampsia and adverse outcomes (Rana et al. 2012).

Even though a reduction of sFlt-1 below a critical threshold has been proposed as therapy (Bergmann A, Ahmad S, Cudmore M, Gruber A D, Wittschen P, Lindenmaier W, Christofori G, Gross V, Gonzalves A, Grone H J, Ahmed A, Weich H A. *J Cell Mol Med*. 2010; 14(6B):1857-1867; Thadhani R, Kisner T, Hagmann H, Bossung V, Noack S, Schaarschmidt W, Jank A, Kribs A, Cornely O A, Kreyssig C, Hemphill L, Rigby A C, Khedkar S, Lindner T H, Mallmann P, Stepan H, Karumanchi S A, Benzing T. *Circulation*. 2011; 124(8):940-950) preeclampsia does not develop in all women with high sFlt-1 (Levine R J, Maynard S E, Qian C, Lim K H, England L J, Yu K F, Schisterman E F, Thadhani R, Sachs B P, Epstein F H, Sibai B M, Sukhatme V P, Karumanchi S A. *N Engl J Med*. 2004; 350(7):672-683; Solomon C G, Seely E W. *N Engl J Med*. 2004; 350(7): 641-642).

In contrast, placental growth factor (PlGF) is reduced in the first trimester of pregnant women who subsequently developed the syndrome. (Torry D S, Wang H S, Wang T H, Caudle M R, Torry R J. *Am J Obstet Gynecol*. 1998; 179(6 Pt 1):1539-1544) (Taylor R N, Grimwood J, Taylor R S, McMaster M T, Fisher S J, North R A. *Am J Obstet Gynecol*. 2003; 188(1):177-182) (Levine R J, Thadhani R, Qian C, Lam C, Lim K H, Yu K F, Blink A L, Sachs B P, Epstein F H, Sibai B M, Sukhatme V P, Karumanchi S A. *Jama*. 2005; 293(1):77-85) (Buhimschi C S, Norwitz E R, Funai E, Richman S, Guller S, Lockwood C J, Buhimschi I A. *Am J Obstet Gynecol*. 2005; 192(3):734-741) (Savvidou M D, Noori M, Anderson J M, Hingorani A D, Nicolaides K H. *Ultrasound Obstet Gynecol*. 2008; 32(7):871-876 (Foidart J M, Munaut C, Chantraine F, Akolekar R, Nicolaides K H. *Ultrasound Obstet Gynecol*. 2010; 35(6):680-687) (Noori M, Donald A E, Angelakopoulou A, Hingorani A D, Williams D J. *Circulation*. 2010; 122(5):478-487). Placental growth factor is recognised as an early diagnostic biomarker and is used alongside sFlt-1 to aid diagnosis of preeclampsia. Commercially available assay kits are produced by Roche Diagnostics under the trade names Electrosys sFlt-1 and Electrosys PlGF immunoassays. This is discussed in the article by Verlohren et al (Am. J. Onstet, Gyne (2010) 161e1), which suggests that the kit may be an aid to diagnosis. The sensitivity for late onset PE is only 58.2%. This assay is also discussed in U.S. Pat. No. 7,407,659. Recently, using these kits, the sFlt-1:PlGF ratio has been measured to predict the short-term absence of preeclampsia in women in whom the syndrome is suspected clinically (Zeisler et al. *N engl j med* 374; 1 nejm.org Jan. 7, 2016).

Heme oxygenase 1 (Hmox1) is the enzyme responsible for the degradation of heme to generate equimolar amount of biliverdin (converted to bilirubin), free iron (to make ferritin, Fe-III-ferritin complexes) and carbon monoxide (CO), a potent vasodilator with anti-apoptotic properties (Gozzelino, Jeney et al. 2010). Stimuli that cause oxidative stress such as peroxynitrite, up-regulate the expression of Hmox1. (Gozzelino et al. 2010, Motterlini et al. 2010). Indeed, human Hmox1 deficiency result in severe and persistent endothelial damage (Yachie et al. 1999), which is also a central phenomenon associated with preeclampsia (Roberts et al. 1989.) The protective function of Hmox1 has been described in human placental tissues, (Ahmed et al. 2000) and Hmox1 negatively regulates sFlt-1 production, (Cudmore et al. 2007) a general phenomenon has been confirmed by many studies. For example, a number of drugs that inhibit sFlt-1 via up-regulation of Hmox1 (Onda et al. 2015,McCarthy et al. 2011); sildenafil suppresses sFlt-1 from trophoblast via Hmox1 (Jeong et al. 2014). In addition, Hmox1 induction attenuates ischemia-induced hypertension in pregnant rats (George et al. 2011) and proteinase-activated receptor-2 mediated sFlt-1 release (Al-Ani et al. 2010). Moreover, diastolic blood pressures and plasma soluble sFlt-1 levels were significantly elevated in Hmox-1$^{+/-}$ pregnant mice (Zhao et al. 2009). Indeed, Hmox1 transcript is decreased in women destined to develop preeclampsia (Farina et al. 2008) and polymorphism in the Hmox1 promoter is associated with preeclampsia, (Kaartokallio et al. 2014) and women with preeclampsia have significantly reduced level of CO in their exhaled breath compared to those with healthy pregnancies indicating a decreased in Hmox1 activity (Baum et al. 2000).

L-arginine acts as a substrate for eNOS and arginase to produce NO and urea respectively. L-arginine availability is a major determinant of NO bioavailability; its reduction increases peroxynitrite formation through scavenging of NO by superoxide anions (Goulopoulou et al. 2015). A decrease in L-arginine and homoarginine levels at 11-13 weeks' gestation was observed in women who developed severe PE (Khalil et al. 2010). A recent study showed that parameters of L-arginine metabolism do not discriminate early-onset from late-onset PE but provided indirect evidence for the redirection of L-arginine-NOS to the L-arginine-arginase pathway (Tamas et al. 2013). Yet why or how arginase activity was increased in preeclampsia is unknown.

Arginase inhibitor or L-arginine supplementation have been used for phase I/II clinical trials such as prevention of ischemia-reperfusion injury in patients with coronary artery disease (NCT02009527, Kovamees et al. 2014) and gastric cancer (Zhao et al. 2013). L-arginine supplementation alone has been used in small clinical trials in pregnancy complications without conclusive outcomes. A study by Vadillo-Ortega and colleagues showed that L-arginine supplementation reduced the risk of preeclampsia in high risk women when administered with antioxidant vitamins, (Vadillo-Ortega et al. 2011) while others showed little or no beneficial effects for treating the disease (Staff et al. 2004). L-arginine supplementation alone also increases the levels of asymmetric dimethylarginine and arginase (Staff et al. 2004), both of which are direct and indirect competitive inhibitors of endothelial NOS and are increased in preeclampsia (Sankaralingam et al. 2010). The use of L-citrulline supplementation has been shown to increase plasma levels of L-arginine, and NO production as efficiently as L-arginine (Schwedhelm et al. 2008) and in the animal model, L-citrulline has been shown to increase the production of endothelial NOS within endothelial cells while limiting the activity of inducible NOS (Wijnands et al. 2012).

Currently, there is no effective preventive or therapeutic strategy available for preeclampsia. Development of diagnosis and new therapies based on better understanding of the underlying mechanisms of the disease is important. The identification and characterisation of the complex and interactive pathways involved now allows the development of new diagnostic and prognostic methods and the identification of efficacious treatments.

The inventors have found that measuring a fetal marker in a sample and comparing to a maternal marker improves the diagnosis and prognosis of preeclampsia. This aids in the identification of subjects at risk of preeclampsia and furthermore identifies subjects who are likely to respond to treatment using the groups of compounds below.

The invention is based on the findings that link low Hmox1 activity and high sFlt-1 levels with increased arginase-1 expression and dysregulation of urea cycle in preeclampsia. The inventors have now found an improved set of diagnostic markers. They have found that the angiogenic factors sFlt-1 and/or PlGF may be measured together with heme and/or arginine breakdown products such as bilirubin and urea respectively. The ratio of sFlt-1 and/or PlGF to breakdown products has now been demonstrated to be a predictive marker for preeclampsia. This unexpected combination provides a link between the fetal-associated markers (sFlt-1 and/or PlGF) and the maternal markers (the heme breakdown products and urea). This ratio therefore provides an indicator based on the welfare of both the mother and the fetus, rather than a marker based solely on the placenta or fetus. A tailored therapy of administration of the combination of L-arginine, an arginase inhibitor and/or citrulline can be provided based on the ratio.

This ratio was unexpectedly identified by the inventors during a study of heme oxygenase-1 (Hmox1).

The invention is based on the hypothesis that preeclampsia arises due to partial loss of VEGF and Hmox1 activity.

To test the idea directly that induction of high sFlt-1 under low Hmox1 activity causes severe preeclampsia, the inventors delivered sFlt-1 systemically to haploinsufficient Hmox1 (Hmox1+/−) pregnant mice by intravenous injection of adenovirus expressing sFlt-1 (Ad-sFlt-1), which increased the level of sFlt-1 in the maternal circulation (FIG. 3). High sFlt-1 levels not only induced higher blood pressure but also a greater degree of renal and liver injury in Hmox1$^{+/-}$ pregnant mice compared to wild-type (Hmox1$^{+/+}$) pregnant animals (FIG. 3). As one of the diagnostic criteria for preeclampsia is hypertension, the inventors measured mean arterial blood (MAP) pressure at day 18.5 gestation in these mice and found them to be severely hypertensive compared to their wild-type littermates at higher sFlt-1 level (FIG. 3a). Another key feature of preeclampsia, glomerular endotheliosis, is a good indicator of widespread maternal endothelial damage (Stillman I E, Karumanchi S A. *J Am Soc Nephrol.* 2007; 18(8):2281-2284), which results in poor filtration and increased protein in the urine after 20 weeks gestation (Moran P, Lindheimer M D, Davison J M. *Semin Nephrol.* 2004; 24(6):588-595). The inventors therefore performed blind analysis of renal histology that revealed lobulation and scarring glomeruli typical of severe glomerular endotheliosis (FIG. 3b). Consistent with the renal damage, urinary albumin excretion was significantly increased in these animals compared to the wild-type controls (FIG. 3c). Further direct evidence for severe renal injury was substantiated by the increase in urinary levels of Kidney Injury Molecule-1 (KIM-1), a specific marker for proximal tubule injury associated with severe preeclampsia, (Burwick R M, Easter S R, Dawood H Y, Yamamoto H S, Fichorova R N, Feinberg B B. *Hypertension.* 2014; 64(4):833-838) (FIG. 3d) and urinary sFlt-1 levels (Buhimschi C S, Norwitz E R, Funai E, Richman S, Guller S, Lockwood C J, Buhimschi I A. *Am J Obstet Gynecol.* 2005; 192(3):734-741) (FIG. 3e). Abnormal liver function test is reported to be associated with an increased risk for adverse maternal outcomes (Kozic J R, Benton S J, Hutcheon J A, Payne B A, Magee L A, von Dadelszen P. *J Obstet Gynaecol Can.* 2011; 33(10):995-1004). Both alanine aminotransferase (ALT) (FIG. 3f) and aspartate aminotransferase (AST) (FIG. 3g), markers of liver function defect, were significantly increased in Hmox1 compromised mice under the high sFlt-1. Interestingly, soluble Endoglin (sEng) reported to induce severe preeclampsia in concert with sFlt-1 (Venkatesha S, Toporsian M, Lam C, Hanai J, Mammoto T, Kim Y M, Bdolah Y, Lim K H, Yuan H T, Libermann T A, Stillman I E, Roberts D, D'Amore P A, Epstein F H, Sellke F W, Romero R, Sukhatme V P, Letarte M, Karumanchi S A. *Nat Med.* 2006; 12(6):642-649) was also increased (FIG. 3h). Consistent with the severe preeclampsia phenotype, reduced fetal growth (FIG. 3i) and increase fetal reabsorption (FIG. 3j) were prominent in Hmox1$^{+/-}$ mice given Ad-sFlt-1.

It is known that increased Hmox1 activity increases plasma concentrations of bilirubin (Hayashi S, Takamiya R, Yamaguchi T, Matsumoto K, Tojo S J, Tamatani T, Kitajima M, Makino N, Ishimura Y, Suematsu M. *Circ Res.* 1999; 85(8):663-671), hence the inventors measured plasma bilirubin as a marker of Hmox1 activity. An unexpected finding was that sFlt-1 induced a dramatic increase in plasma bilirubin in the wild-type pregnant mice (FIG. 3l), but the increase in plasma bilirubin in Hmox1$^{+/-}$ mice was blunted (FIG. 3l) raising the possibility that high sFlt-1 induces Hmox1 activation as a stress response mechanism in the wild-type animals. These discoveries by the inventors during these studies provided the inventive step to consider that high sFlt-1 and low Hmox1 activity produce a severe form of preeclampsia and this could now be used as a diagnostic test for a tailored therapy development.

Loss of Hmox1 under high sFlt-1 levels environment caused a severe form of preeclampsia due to an elevation in arginase activity, decrease in argininosuccinate lyase (Asl) and argininosuccinate synthetase (Ass) expression, which caused a dysregulation of the arginine metabolism (urea cycle), leading to an increase in tissue nitrosative stress (FIG. 4). In addition, increased renal iron overload was observed in Hmox1$^{-/-}$ mice with high levels of sFlt-1 (FIG. 9). The observed dysregulation in the urea pathway was mirrored in women with severe preeclampsia, who displayed abnormally high sFlt-1 and low bilirubin (FIG. 7). In this validation group of patients, placental arginase was dramatically increased at both mRNA (FIG. 7d) and protein levels (FIG. 7g). In contrast, transcript and protein levels of Asl (FIG. 7e, 7g, 7j) and Ass1 (FIG. 7f, 7g, 7k) were significantly decreased. In early onset patients, the ratios between sFlt-1 and bilirubin showed an area under the receiver operating characteristic (ROC) curves statistically difference from 0.97 (FIG. 7m). Furthermore, in patients with a singleton pregnancy presenting after 20+0 weeks of gestation with signs of suspected preeclampsia, levels of urea, the product of arginine hydrolysis by arginase, were significantly increased while bilirubin levels were decreased (FIG. 8). The ratios between sFlt-1/PlGF and bilirubin/Urea were proven to have important predictive value with a sensitivity of 91.67% and specificity of 96% for early onset disease and a sensitivity of 85.7%, specificity of 96% for late onset of the disease (FIG. 8f). The mechanism that leads to increased arginase in preeclampsia is due to loss of Hmox1 expression or activity and high sFlt-1.

To rectify the preeclamptic symptoms, arginase inhibitor (N-ω-Hydroxy-L-norarginine) together with L-arginine were administrated in Hmox1 deficient mice in the presence of high sFlt-1. The treatments resulted in reduced renal glomerulosclerosis and mesangiolysis (FIG. 5a-5b), proteinuria (FIG. 5c) and urinary levels of KIM-1 (FIG. 5d) following injury caused by high sFlt-1. Nitrosative stress was reduced, where renal 3-nitrotyrosine immunostaining appeared diminished following treatment (FIG. 5e). These improvements were absent when L-arginine or the arginase inhibitor was given alone (FIG. 5a-5c). Placental arginase transcript was upregulated in the Hmox1$^{+/-}$ pregnant mice after sFlt-1 exposure (FIG. 5e) and arginase inhibitor combined with L-arginine supplementation in Hmox1$^{+/-}$ pregnant animals rescued the preeclampsia-like symptoms, including hypertension (FIG. 5f), proteinurea (FIG. 5g), urinary Kim-1 levels (FIG. 5h) and fetal reabsorption rate (FIG. 5i). Fetal weight increased (FIG. 5j) and looked normal after treatment (FIG. 5k). Administration of an arginase inhibitor or L-arginine supplementation alone failed to abolish all signs of preeclampsia (FIG. 5f-5j) in these animals. In addition, an arginase inhibitor and L-arginine combined administration in reduced uterine perfusion pressure (RUPP) model of preeclampsia was also proven to be effective (FIG. 6). The invention of a new treatment for preeclampsia may improve preeclamptic symptoms, such as normalisation of blood pressure, decrease in proteinuria and renal damage and improvement in fetal growth and inhibition of fetal reabsorption. The data provides direct evidence that preeclampsia arises from the dysregulation of Hmox1 and arginine metabolism and suggests that upregulation of Hmox1 and downregulation of arginase protects from the clinical signs of preeclampsia.

A first aspect of the invention provides a method of diagnosis or prognosis of preeclampsia in a pregnant subject, comprising providing a sample from a pregnant subject and measuring the ratio between the amount of (a) one or both of sFlt-1 and PlGF, and (b) one or both of a breakdown product of heme and a breakdown product of arginine, in the sample.

When measured alone, sFlt-1 has been specially used as a suitable marker in the diagnosis of late onset preeclampsia, especially when measured in combination with and compared to a heme breakdown product, such as bilirubin.

sFlt-1 and PlGF may also be measured together to provide a ratio, which is especially useful in indicating late onset preeclampsia when measured in combination with and compared to a heme breakdown product, such as bilirubin.

sFlt-1 and PlGF may also be measured together to provide a ratio, in combination with a heme breakdown product, such as bilirubin, and an arginine breakdown product, such as urea, which also may be measured together to provide a ratio, and these two ratios may be compared with one another. This is especially useful in indicating late onset preeclampsia.

sFlt-1, PlGF, a heme breakdown product such as bilirubin and an arginine breakdown product such as urea may also be measured together to provide a ratio, which is especially useful in indicating late onset preeclampsia.

Arginine breakdown products may include urea, ornithine, citrulline, arginosuccinic acid and ammonia. Urea is a hydrolysis product of arginine by arginase (see FIG. 2), and the blood level of urea is highly correlated with arginase activity (Liener et al. 1950), so it is expected to be found in higher concentrations than normal in subjects at risk of preeclampsia.

The invention may additionally measure the amount of arginine and arginase expression and activity in a sample from the subject.

A further aspect of the invention provides a method of diagnosis or prognosis of preeclampsia in a pregnant subject comprising providing a sample from a pregnant subject and measuring the ratio between the amount of sFlt-1 and a marker of kidney or renal function in the sample. The marker of kidney or renal damage may be KIM-1 (urinary kidney injury molecule 1).

The ratio may be compared to a predetermined ratio to determine the prognosis or diagnosis of preeclampsia. Typically an increase in the ratio above a certain level indicates that the subject has preeclampsia and has a poor prognosis of the preeclampsia.

Methods of monitoring preeclampsia in a subject by monitoring the ratio in samples taken from the subject are also provided.

The heme breakdown pathway involves Hmox1. FIG. 1 is adapted from the article by Ryter S. W. et al (Physiol. Rev. (2006) 86, 583-650) and summarises the breakdown products of heme.

As shown in FIG. 1, Hmox1 breaks down heme into free iron (to make ferritin, Fe-III-ferritin complexes), carbon monoxide, biliverdin (convert to bilirubin). Hence, one or more of those products may be assayed, most typically bilirubin.

The assay may also be used in combination with an assay for placental growth factors (PlGF) to further improve the accuracy of the diagnosis. As already discussed, assays for PlGF are generally known in the art.

Typically the normal levels of sFlt-1 (first trimester: 1107 pg/ml; second trimester: 1437 pg/ml; third trimester: 2395 pg/ml) and bilirubin (first trimester: 1.7-6.8 µmol/dL; second trimester: 1.7-13.7 pmol/dL; third trimester: 1.7-18.8 µmol/dL) are found in healthy subjects without preeclampsia. Typically the normal ratio is less than 239 pg/µmol in blood.

A ratio of above 725 pg/µmol suggests PE in the subject.

Typically the normal levels of PlGF (30-626 pg/ml) are found in healthy subjects without preeclampsia.

A level of less than typically 279 pg/ml of PlGF at second trimester provides further evidence of PE.

Typically the normal levels of urea (2.5-7.1 mmol/dL) are found in healthy subjects without preeclampsia. Typically the normal ratio between sFlt-1:PlGF vs bilirubin:urea is less than 10 in blood.

Typically the normal ratio between sFlt-1:PlGF vs bilirubin is less than 3.3 in blood.

Typically the normal ratio between sFlt-1:PlGF vs urea is less than 5.2 in blood.

Typically the normal ratio between sFlt-1:urea is less than 1020 in blood.

Typically the normal ratio between sFlt-1 vs bilirubin:urea is less than 698.4 in blood.

Typically the normal ratio between PlGF vs bilirubin:urea is more than 161.4 in blood.

Typically the normal ratio between PlGF vs bilirubin is more than 33.94 in blood.

Typically the normal ratio between PlGF vs urea is more than 45.09 in blood.

The preeclampsia may be early- or late-onset of the disease.

The sFlt-1, PlGF, heme breakdown product or arginine breakdown product may be measured using an analyte specific binding agent such as an antibody or fragment thereof, such a Fab, $F(ab')_2$ or svFv. The sFlt-1 or heme breakdown product may be determined by immunoassay such as ELISA or other immunoassays generally known in the art.

Typically CO levels could be measured in exhaled breath using CO breath analyser or from blood serum or plasma sample analysis.

Bilirubin may be measured, for example, using Diazo method, high performance liquid chromatography, enzymatically via the conversion of bilirubin oxidase or spectrophotometrically at 473 nm, the maximum absorbance of bilirubin from blood serum or plasma sample.

Biliverdin may be measured, for example, using infrared fluorescence, spectrophotometrically or through the measurement of Biliverdin reductase activity assay from blood serum or plasma sample.

Ferritin levels can be measured using immunoassays or immunoradiometric methodology on assay platforms such as Abbott Architect or Roche ECLIA from blood serum or plasma sample.

Typically, arginine or urea may be measured using high-performance liquid chromatography, or measured using a specific binding agent such as an antibody or fragment thereof, such a Fab, $F(ab')_2$ or svFv. Levels may be determined by immunoassay such as ELISA or other immunoassays generally known in the art.

Arginase may be measured using specific binding agent such as an antibody or fragment thereof, such a Fab, $F(ab')_2$ or svFv. Levels may be determined by immunoassay such as ELISA or other immunoassays generally known in the art.

Arginase activity may be measured spectrophotometrically from blood serum or plasma sample. The urea produced specifically reacts with the substrate to generate a colored product, proportional to the arginase activity present.

The sample may be a sample of blood, urine, serum or plasma. A pregnant human subject may provide it. It may be provided, for example, at week 20 of pregnancy, when the mother typically also has an ultrasound scan taken. Alternatively, it may be provided at other times during pregnancy to monitor, for example, pre-existing PE or to see if treatment of PE is being effective. The sample may be separated and used in different assays. Alternatively different samples may be used for different analytes. Hence Blood may be used for one analyte and urine for another one.

Assay kits for use in the methods of the invention are also provided.

They typically comprise a specific binding agent and one or more agents to specifically detect a breakdown product of heme, such as a specific binding agent. The specific binding agent may be an antibody or a fragment thereof as defined above. The heme breakdown product may be as defined above.

The assay kit may comprise an assay kit component specific for the analysis of the heme breakdown product, for example bilirubin oxidase for the detection of bilirubin or biliverdin reductase for the detection of biliverdin.

The assay kit may comprise components specific for the analysis of the arginine hydrolysis product, such as urea.

Hmox1 dysregulation has been found by the inventors to cause dysregulation of the arginine metabolism (part of the urea cycle) under high sFlt-1 levels leading to an elevation of arginase activity, for example, arginase I or II activity, decrease in argininosuccinate lyase (Asl) and argininosuccinate synthetase (Ass) expression, which causes a dysregulation of eNOS/urea pathway in kidney and placenta. The urea cycle pathway is summarised in FIG. 2.

This has now been identified by the inventors as being rectifiable.

A further aspect of the invention provides a method of treating preeclampsia, comprising administering a pharmaceutically effective amount of L-arginine and/or citrulline and an inhibitor of arginase or activators of argininosuccinate lyase (Asl) and argininosuccinate synthetase (Ass).

Arginase inhibitors are known in the art. For example, the inhibitor may be nor-NOHA (N-hydroxy-nor-arginine). This has been previously used to restore endothelial function in ischemic injury (Kovamees O. et al PLOS one (2014, 9(7) e103260). The inhibitor was delivered intravenously. For example, the inhibitor may be an arginase I or II inhibitor.

L-arginine treatment with and without antioxidant vitamin supplements is known in the art. For example L-arginine has been given to pregnant women with preeclampsia (Vadillo-Ortega F. et al BMJ (2011, 342:d2901).

Typically L-arginine is administered with an arginase inhibitor.

L-citrulline treatment has also been tested and L-citrulline protects from kidney damage in type1 diabetic mice (Romero M J et al Frontiers of Immunology (2013, 4: doi: 10.3389/fimmu.2013.00480).

Methods of treating preeclampsia using the combinations of:
(i) citrulline and an activator of ASI and ASS; or
(ii) arginosuccinic acid and an activator of ASS; are also provided. These are components of the pathway shown in FIG. 8 and are expected to be able to treat preeclampsia.

The combination of arginase inhibitor and L-arginine has also previously been used to treat asthma, sickle cell disease and pulmonary hypertension (EP 2,397,128).

Other arginase inhibitors that may be used include N(omega)-hydroxy-nor-L-arginine (NOHA), 2(S)-amino-6-boronohexanoic acid (ABH), S-(+)-amino-5-C-iodoacetamidohexanoic acid, S-(+)-amino-5-iodoacetamidopetanoic acid, L-norvaline and L-HO Arg. Typically the inhibitor is nor-NOHA or NOHA.

L-arginine and/or citrulline and an inhibitor of arginase for use in the treatment of preeclampsia, is also provided. Typically L-arginine is administered in combination with an inhibitor of arginase.

Typically L-arginine or citrulline may be administered orally, but may also be administered by injection, for example, in combination with the inhibitor of arginase.

The arginase inhibitor may be administered orally, but more typically by injection.

Injection may be intravenously, subcutaneously, intramuscularly or intraperitoneally.

The patient to be treated may have been identified using a method according to the invention.

The methods of treatment of the invention work especially well with patients who have a high sFlt-1 and/or PlGF to heme breakdown product and/or arginine product ratio in their body, such as in blood, serum, plasma or urine. Hence the patient may be one with such a high ratio.

The invention also provides a method of treating preeclampsia, comprising administering a pharmaceutically effective amount of L-arginine and/or citrulline and an inhibitor of arginase and an iron chelating agent, such as Deferoxamine. Increased renal iron overload may be observed in patients with high levels of sFlt-1, and iron chelating agents may be used to counteract this.

Computers and analytical devices comprising the means for calculating the method of diagnosis, prognosis and monitoring as defined above are also provided.

The computer may be adapted to provide receiving a signal indicating an amount of (i) sFlt-1 and/or PlGF in a sample from a pregnant subject and (ii) a signal indicating an amount of a heme breakdown product and/or arginine breakdown product (iii) a signal indicating a kidney function or liver function marker in a sample from a pregnant subject and means for comparing the signals to produce a ratio and a display for displaying the ratio. The markers and methods of detecting the markers may be as defined above.

The computer may comprise a read only memory.

The signal may be, for example, a signal indicating a colour from an assay for one of the components. This may be compared to a predetermined concentration curve in the computer to calibrate the amount of the analyte and then produce the ration when compared to the second analyte.

All anti-VEGF drugs given to cancer patients can induce a 'preeclampsia-like syndrome' (Vigneau, C. et al. 2014).

The Inventors provide a new therapy to reduce the "preeclampsia like signs in cancer patients receiving anti-VEGF therapy as they have delineated the pathophysiological pathway for 'the preeclampsia phenotype'. They will add the use of dual-therapy (L-arginine+Arginase inhibitor) in the treatment of cancers where cancer patients are or will be treated with VEGF neutralizing antibodies (such as Avastin), VEGF receptor antagonists (such as sorafenib, sunitinib and brivanib) and VEGF trap (such as Aflibercept).

In all diseases or therapies, which result in imbalance in angiogenic activity and antioxidant enzyme activity, the inventors' dual-therapy (L-arginine+Arginase inhibitor) is proposed to reduce symptoms or side-effects of ongoing therapy.

A further aspect of the invention uses L-arginase and arginase inhibitors (for example as defined above) to reduce the side-effects of anti-VEGF compounds in the treatment of cancer.

The invention provides a method of treating cancer, comprising treating a subject with a therapeutically effective amount of an anti-VEGF compound and L-arginine and an arginase inhibitor for use in the treatment of cancer, is also provided.

VEGF (Vascular Endothelial Growth Factor) is a signal protein produced by cells that stimulate vasculogenesis and angiogenesis. Cancers expressing VEGF are able to grow and metastasize. Inhibiting VEGF or its effects are therefore a way of treating cancer.

The anti-VEGF compound may be an anti-VEGF antibody, or functional fragment thereof. These include Bevacizumab (humanized monoclonal antibody against VEGF-A) and VEGF-Trap (decoy VEGF receptor eg Aflibercept) block the activity of circulating VEGF, whereas sorafenib, sunitinib and brivanib are multi-target tyrosine kinase inhibitors (MTKIs) of the VEGF signalling pathway (especially the VEGF receptors).

The invention will now be described by way of example only, with reference to the following figures.

Figure 1:
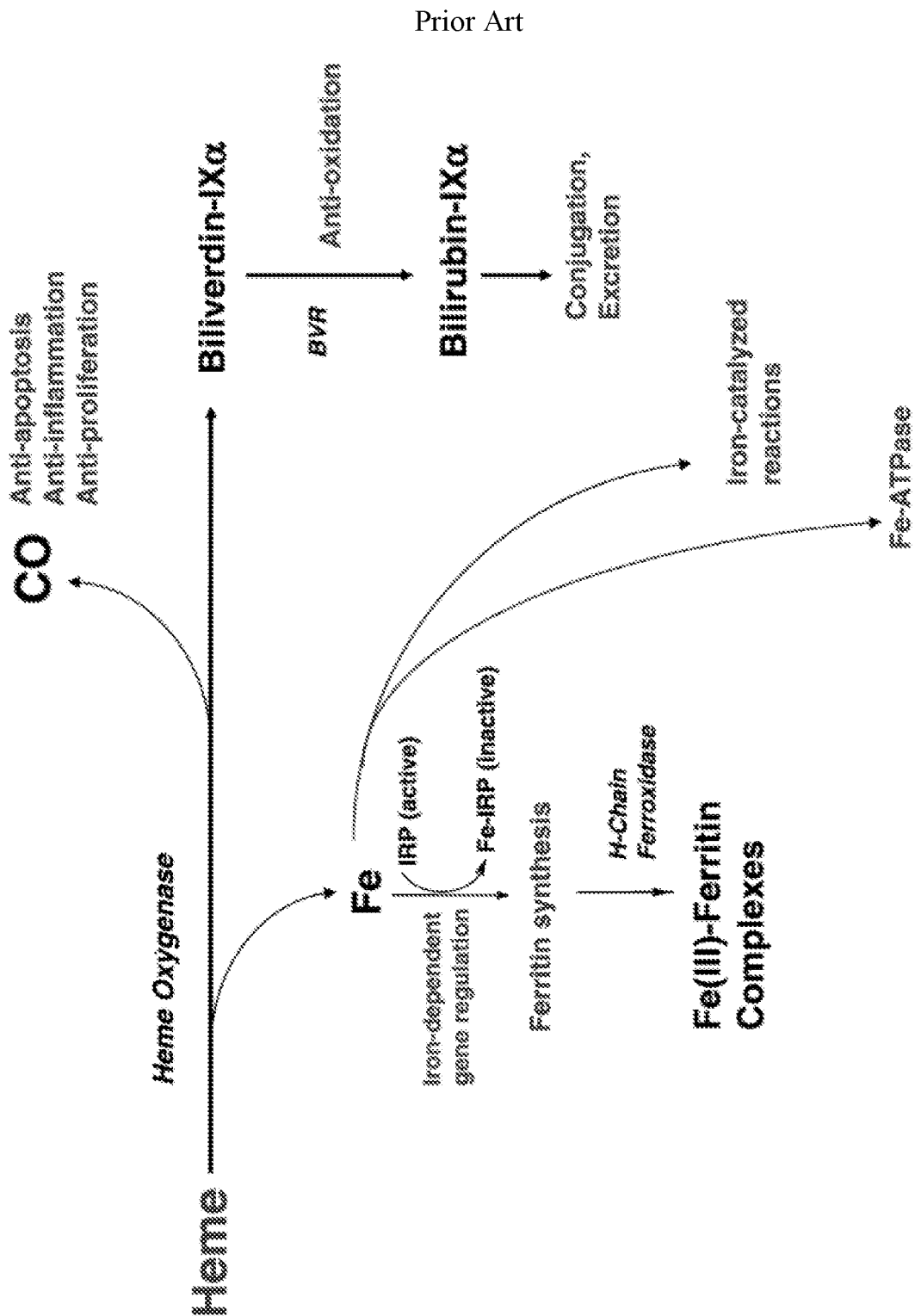
FIG. 1 shows the heme breakdown pathway (adapted from Ryter et al Physiol. Rev. (2006) 86, 583-650).
Figure 2:
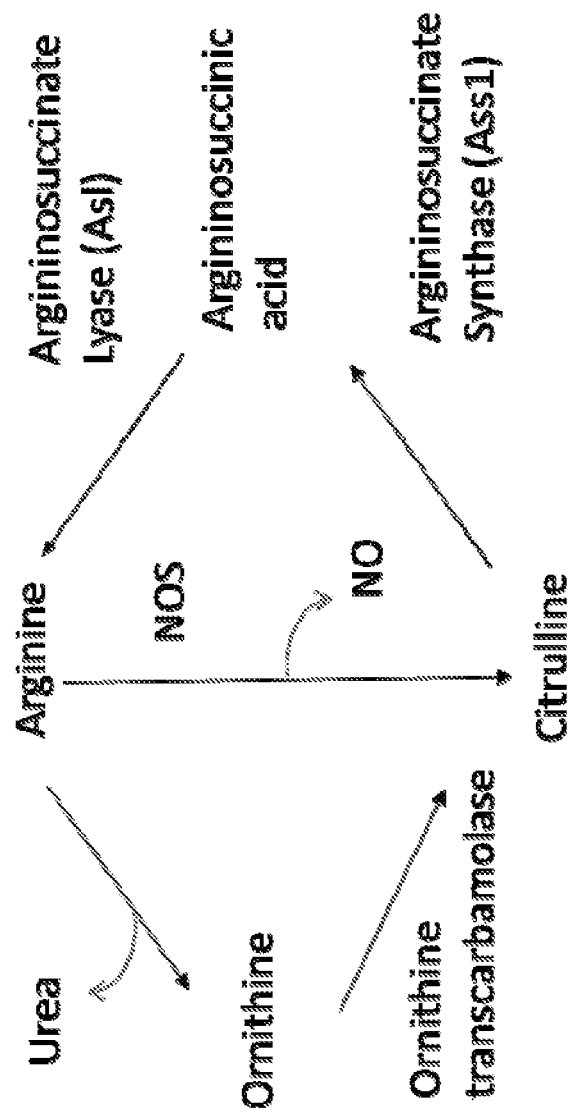
FIG. 2 shows the arginine pathway a part of the Urea Cycle.
Figure 3:
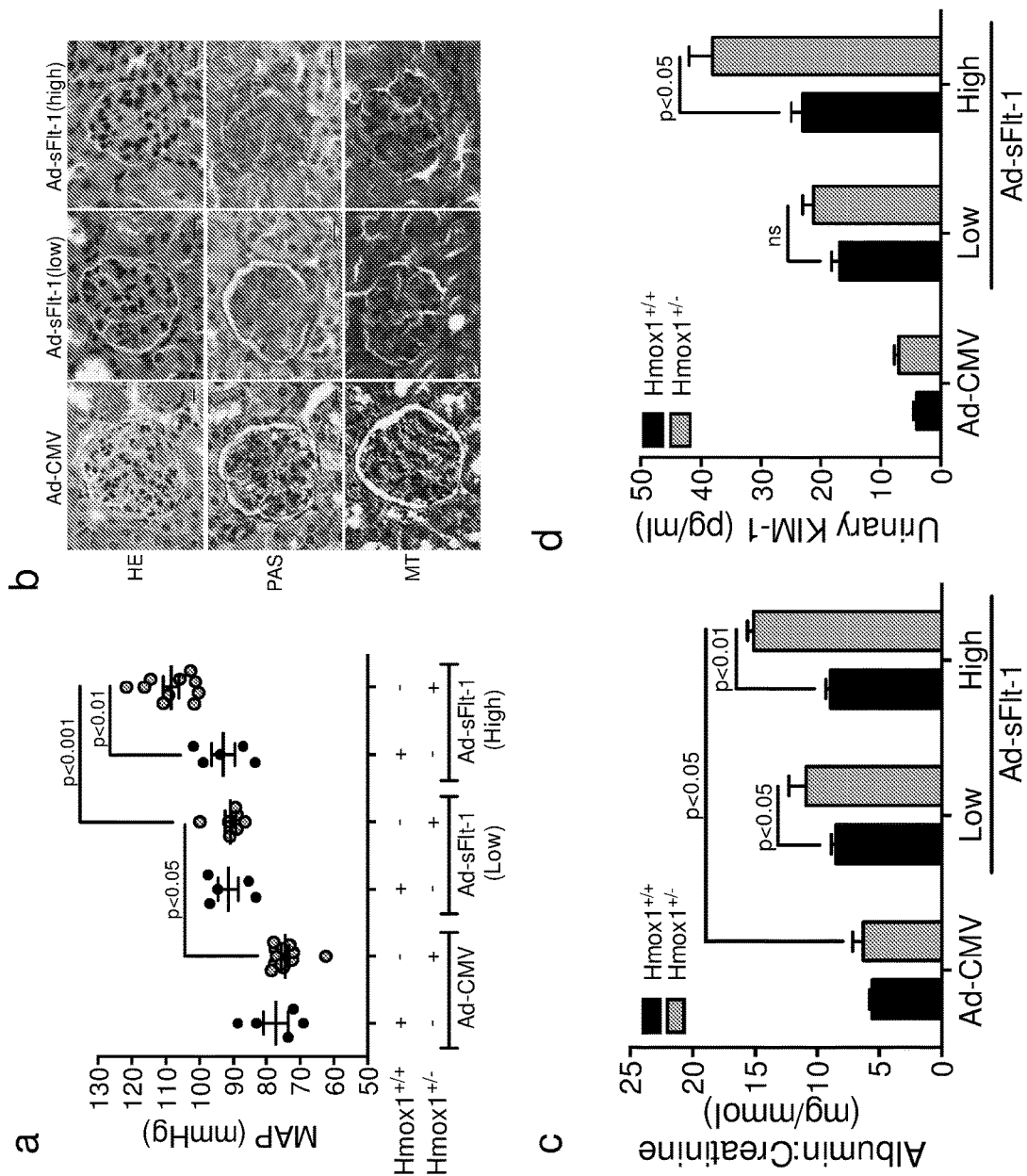
Figure 3:
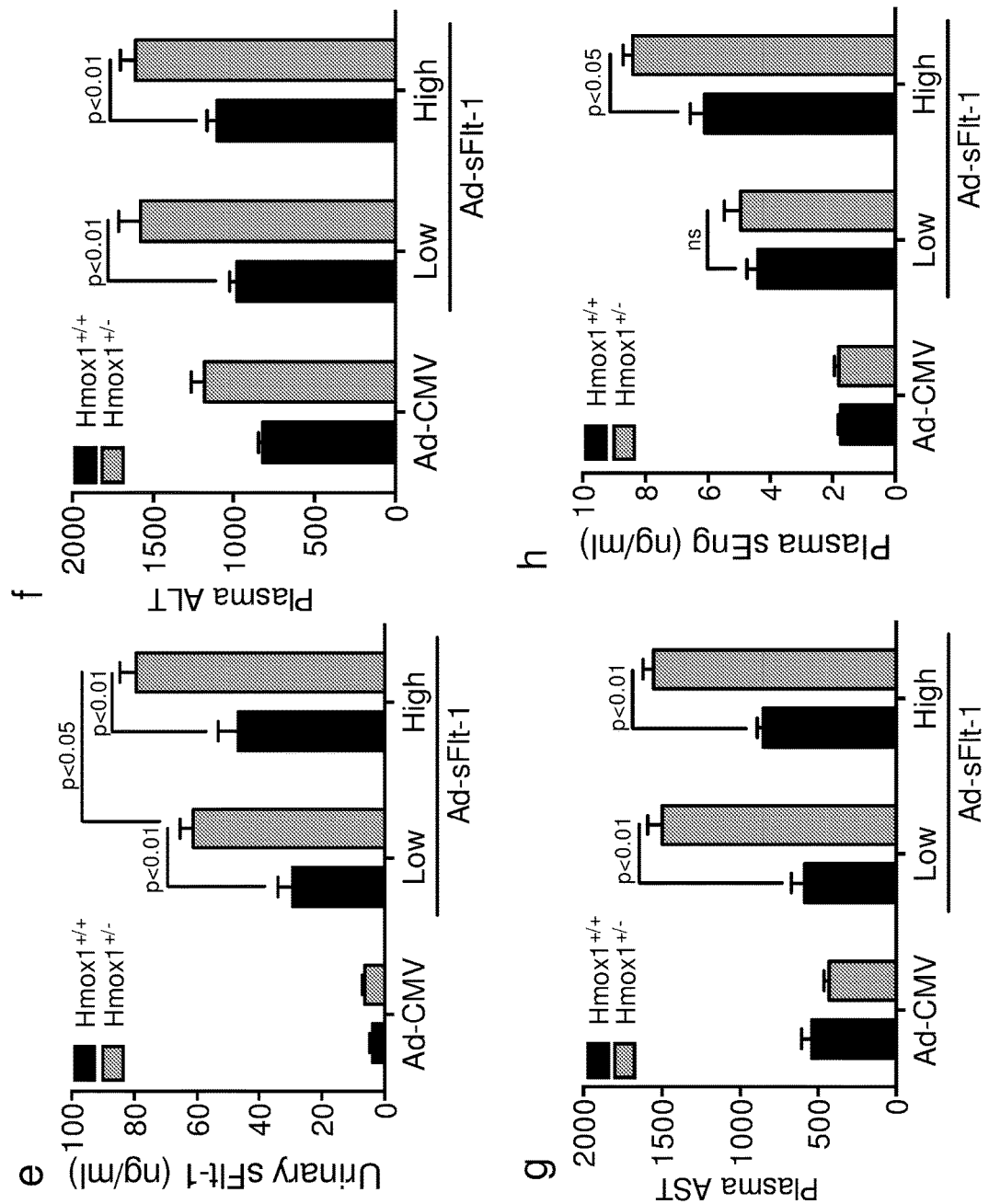
Figure 3:
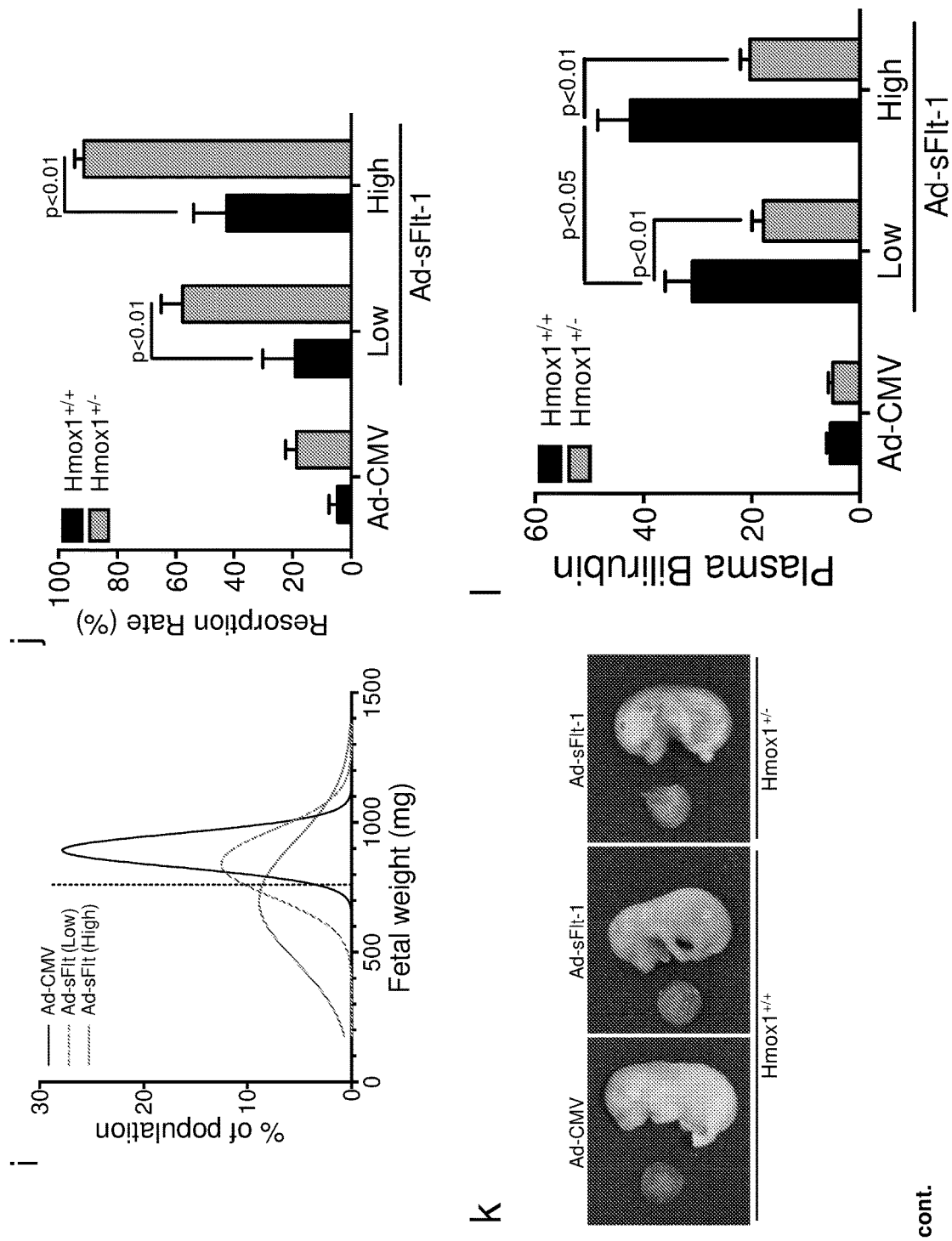

FIG. 3. Partial Hmox1 deficiency leads to severe preeclampsia in pregnant Hmox1$^{+/-}$ mice under high sFlt-1 environment. (A) Mean arterial blood pressure (MAP) recorded at day 18 of gestation in timed pregnant Hmox1$^{+/-}$ and Hmox1$^{+/+}$ mice treated with two different doses (low dose of 0.5×10$^9$ pfu or high dose of 1×10$^9$ pfu) of Ad-sFlt-1. Ad-CMV served as control group. (B) Representative glomeruli from timed pregnant Hmox1$^{+/-}$ mice treated with low and high doses of Ad-sFlt-1 or control virus. Serial sections were stained with Hematoxylin and Eosin (HE), Periodic acid-Schiff (PAS) or Masson's trichrome (MT). (C) 24 h urinary albumin excretion normalised to urinary creatinine and expressed as a urinary albumin:creatinine ratio at day 18 of gestation from timed pregnant Hmox1$^{+/-}$ and Hmox1$^{+/+}$ mice treated with low and high dose of Ad-sFlt-1 or control virus. (D) Urinary Kidney Injury Molecule-1 (pg/ml) (KIM-1) at day 18 of gestation from timed pregnant Hmox1$^{+/-}$ and Hmox1$^{+/+}$ mice treated with low and high dose of Ad-sFlt-1 or control virus. (E) Urinary sFlt-1 (ng/ml) at day 18 of gestation from timed pregnant Hmox1$^{+/-}$ and Hmox1$^{+/+}$ mice treated with low and high dose of Ad-sFlt-1 or control virus. (F) Plasma alanine transaminase (ALT) at day 18 of gestation from timed pregnant Hmox1$^{+/-}$ and Hmox1$^{+/+}$ mice treated with low and high dose of Ad-sFlt-1 or control virus. (G) Plasma aspartate aminotransferase (AST) at day 18 of gestation from timed pregnant Hmox1$^{+/-}$ and Hmox1$^{+/+}$ mice treated with low and high dose of Ad-sFlt-1 or control virus. (H) Plasma soluble endoglin at day 18 of gestation from timed pregnant Hmox1$^{+/-}$ and Hmox1$^{+/+}$ mice treated with low and high dose of Ad-sFlt-1 or control virus (I) Average fetal weight expressed as grams per pup at day 18 of gestation from timed pregnant Hmox1$^{+/-}$ and Hmox1$^{+/+}$ mice treated with low and high dose of Ad-sFlt-1 or control virus. (J) Total fetal resorption rate expressed as percentage at day 18 of gestation from timed pregnant Hmox1$^{+/-}$ and Hmox1$^{+/+}$ mice treated with low and high dose of Ad-sFlt-1 or control virus. (K) Representative pups and placentas at day 18 of gestation from timed pregnant Hmox1$^{+/+}$ mice treated with high dose Ad-sFlt-1 or Ad-CMV and Hmox1$^{+/-}$ mice treated with high dose of Ad-sFlt-1. (L) Plasma bilirubin at day 18 of gestation from timed pregnant Hmox1$^{+/-}$ and Hmox1$^{+/+}$ mice treated with low and high dose of Ad-sFlt-1 or control virus. Results are representative or expressed as mean (±SEM) and analysed by 1-way repeated-measures ANOVA followed by Student-Newman-Keuls post hoc tests.

Figure 4:
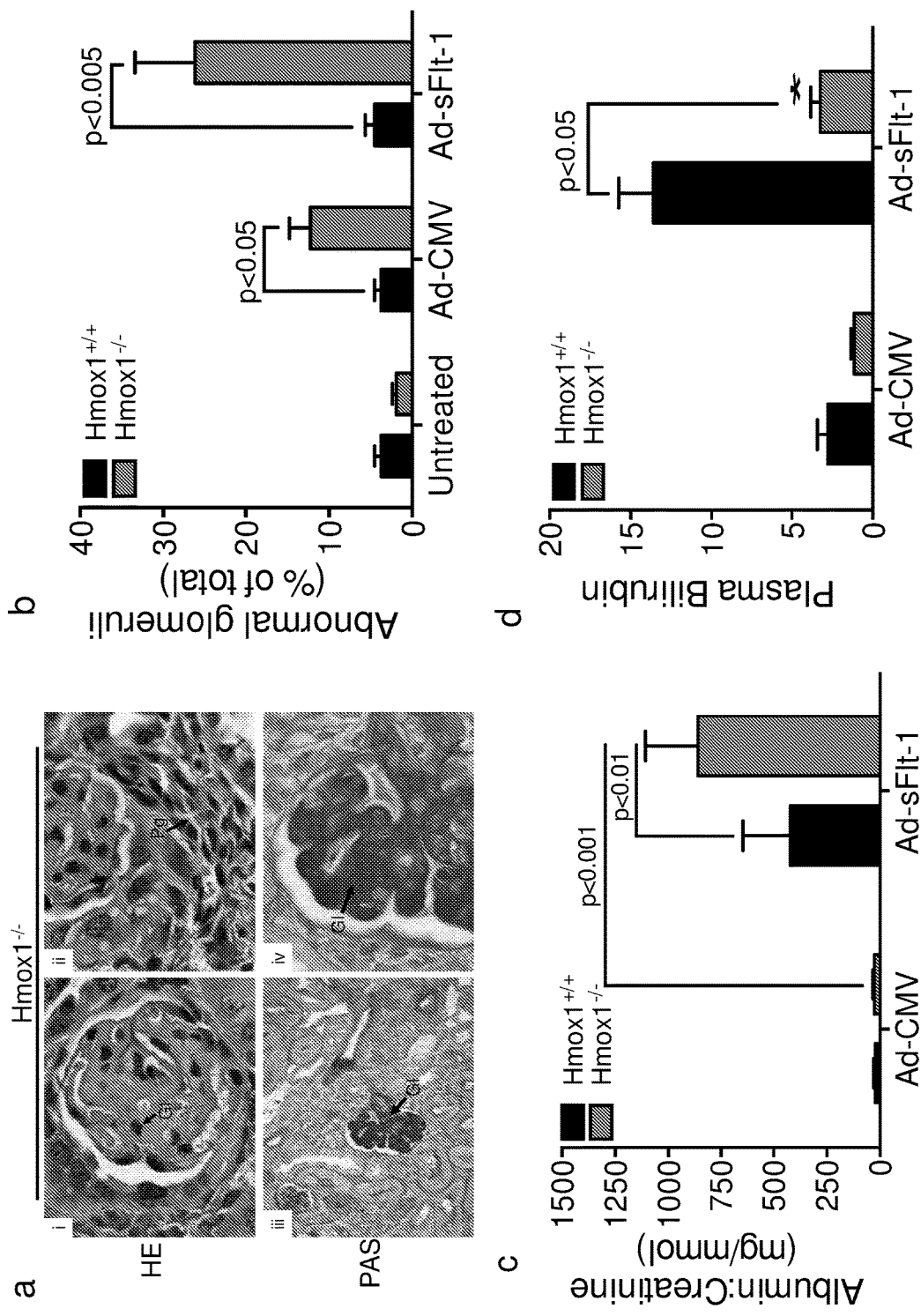
Figure 4:
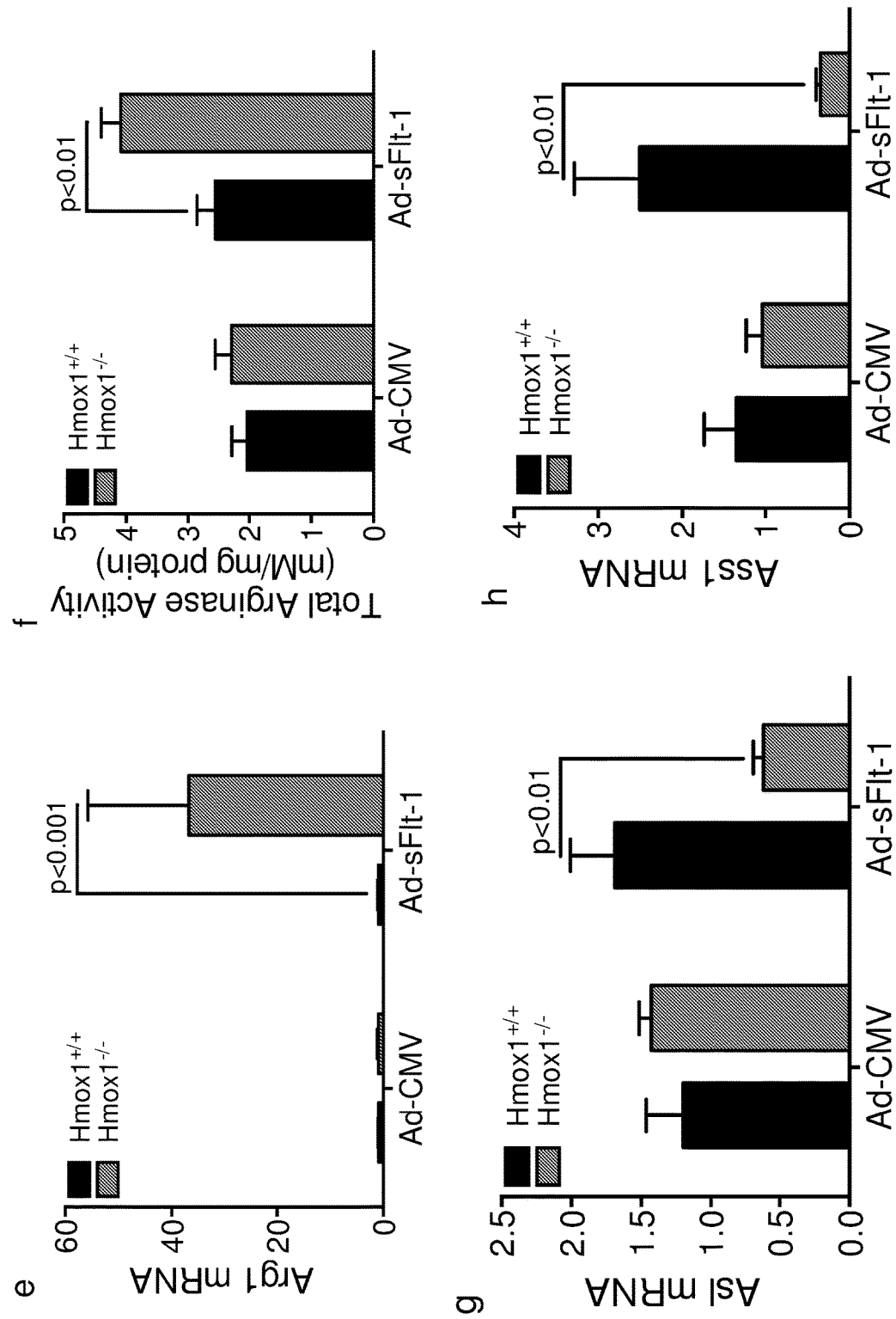
Figure 4:
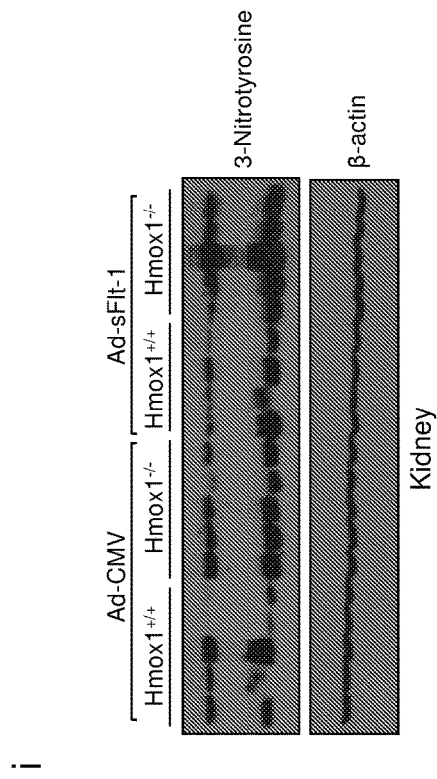

FIG. 4. Soluble Flt-1 exacerbates severe renal damage, dysregulates arginine metabolism and promotes oxidative stress in Hmox1$^{-/-}$ mice. (A) Representative glomeruli from Hmox1$^{-/-}$ mice treated with Ad-sFlt-1 showing severe glomerulosclerosis and mesangiolysis. Serial sections were stained with Hematoxylin and Eosin (HE) and Periodic acid-Schiff (PAS). (B) Blind scoring of the coded slides for abnormal glomeruli and expressed as percentage of total glomeruli per serial section from Hmox1$^{-/-}$ mice treated with Ad-sFlt-1 or control virus (Ad-CMV). (C) 24 h urinary albumin excretion normalised to urinary creatinine and expressed as a urinary albumin:creatinine ratio (ACR) from Hmox1$^{+/+}$ and Hmox1$^{+/-}$ mice treated with Ad-sFlt-1 or control virus. (D) Plasma bilirubin in Hmox1$^{+/+}$ and Hmox1$^{-/-}$ mice treated with Ad-sFlt-1 or control virus. Inset: Western blot showing expression of kidney Hmox1 in Hmox1+$^{+/+}$ mice treated with Ad-CMV or Ad-sFlt-1. (E) Relative mRNA expression of Arginase-1 in kidney lysates of Hmox1$^{+/+}$ and Hmox1$^{-/-}$ mice treated with Ad-sFlt-1 or control virus. (F) Total Arginase-1 activity expressed as mM/mg protein in kidney lysates of Hmox1$^{+/+}$ and Hmox1$^{-/-}$ mice treated with Ad-sFlt-1 or control virus. (G) Relative mRNA expression of argininosuccinate lyase (Asl) in kidney lysates of Hmox1$^{+/+}$ and Hmox1$^{-/-}$ mice treated with Ad-sFlt-1 or control virus (Ad-CMV). (H) Relative mRNA expression of argininosuccinate synthase-1 (Ass1) in kidney lysates of Hmox1$^{+/+}$ and Hmox1$^{-/-}$ mice treated with Ad-sFlt-1 or control virus (Ad-CMV). (I) Western blot showing 3-Nitrotyrosine expression in kidney lysates of Hmox1$^{+/+}$ and Hmox1$^{--}$ mice treated with Ad-sFlt-1 or control virus. β-actin was used as a loading control. Results are representative or expressed as mean (±SEM) and analysed by 1-way repeated-measures ANOVA followed by Student-Newman-Keuls post hoc tests.

Figure 5:
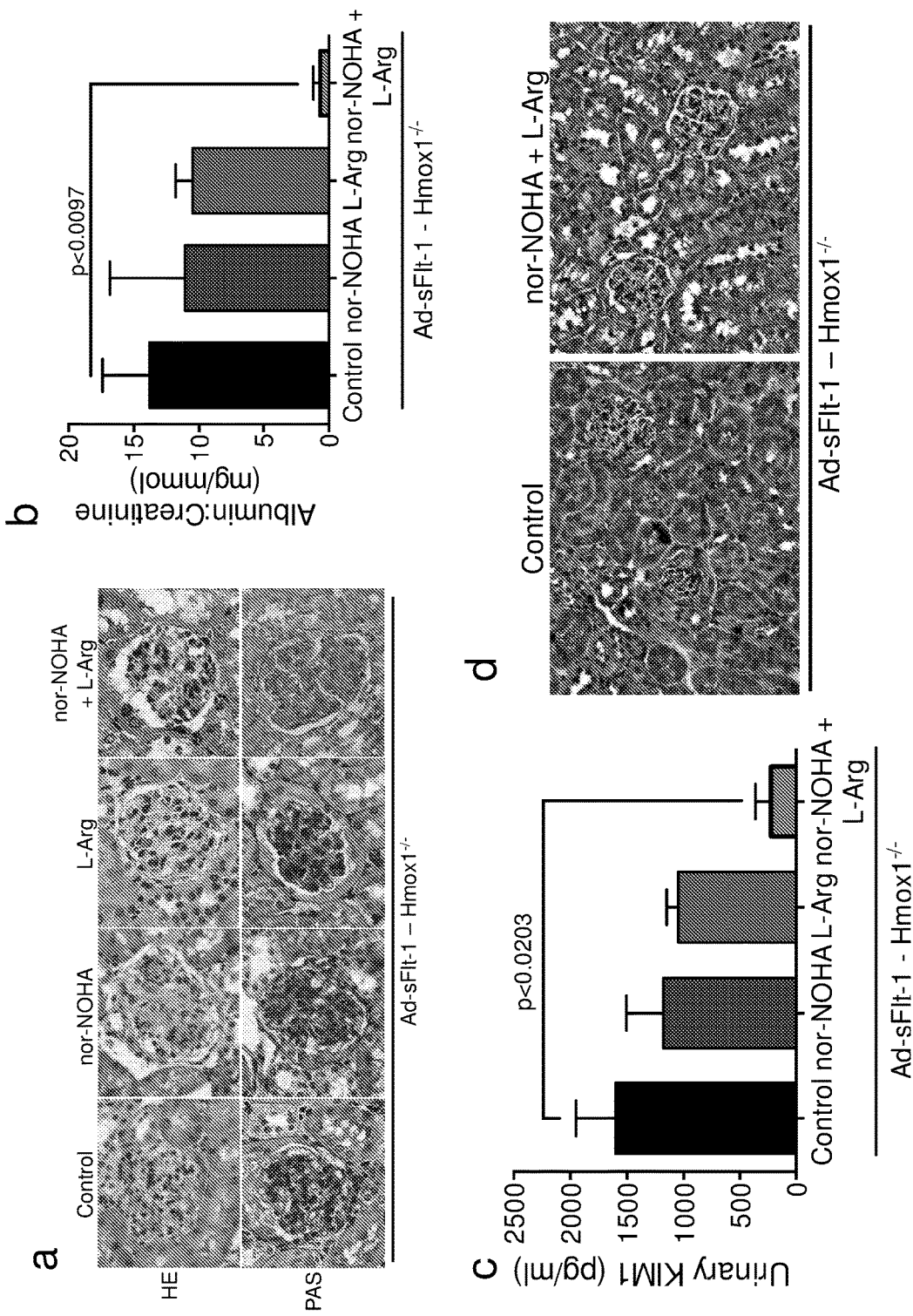
Figure 5:
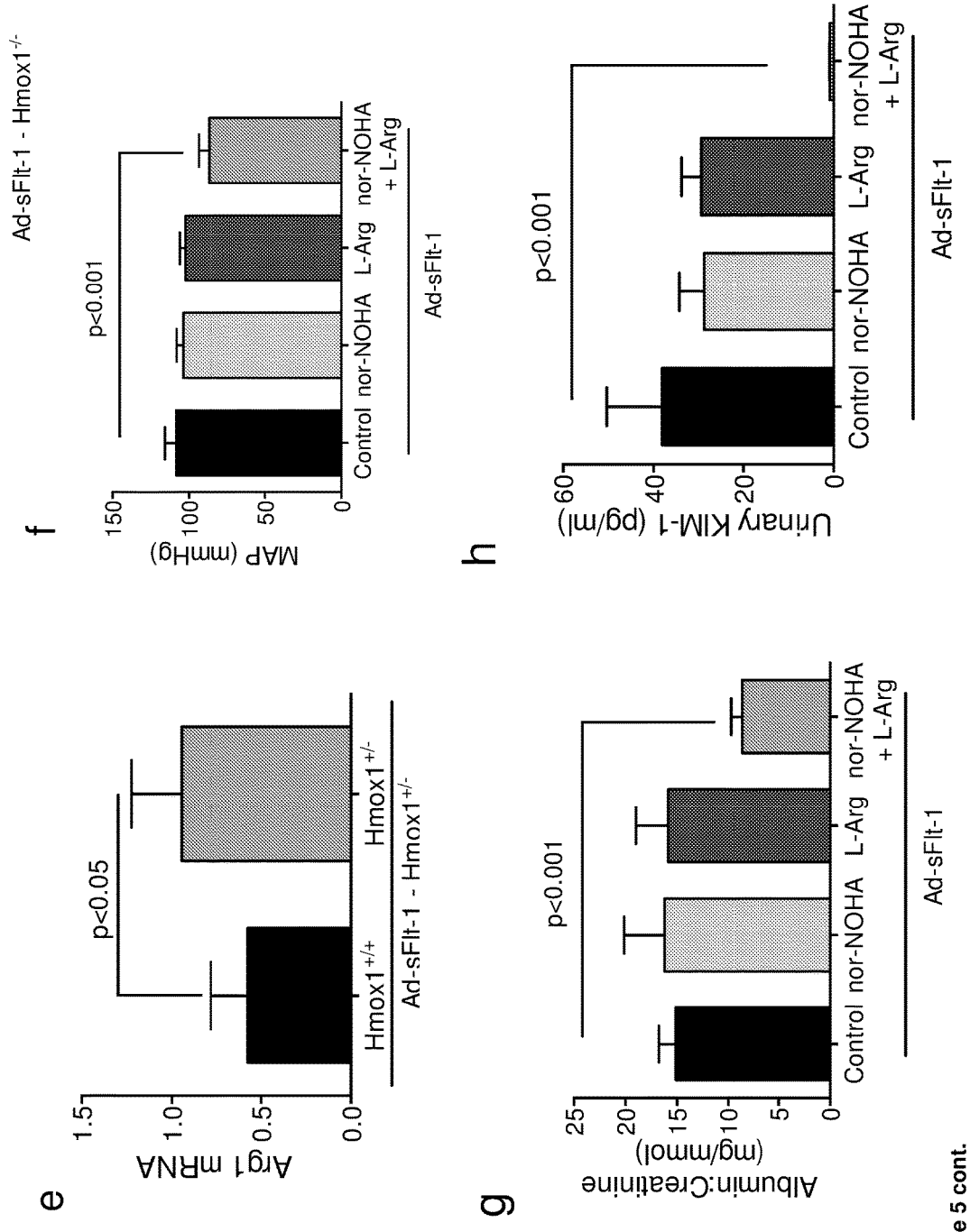
Figure 5:
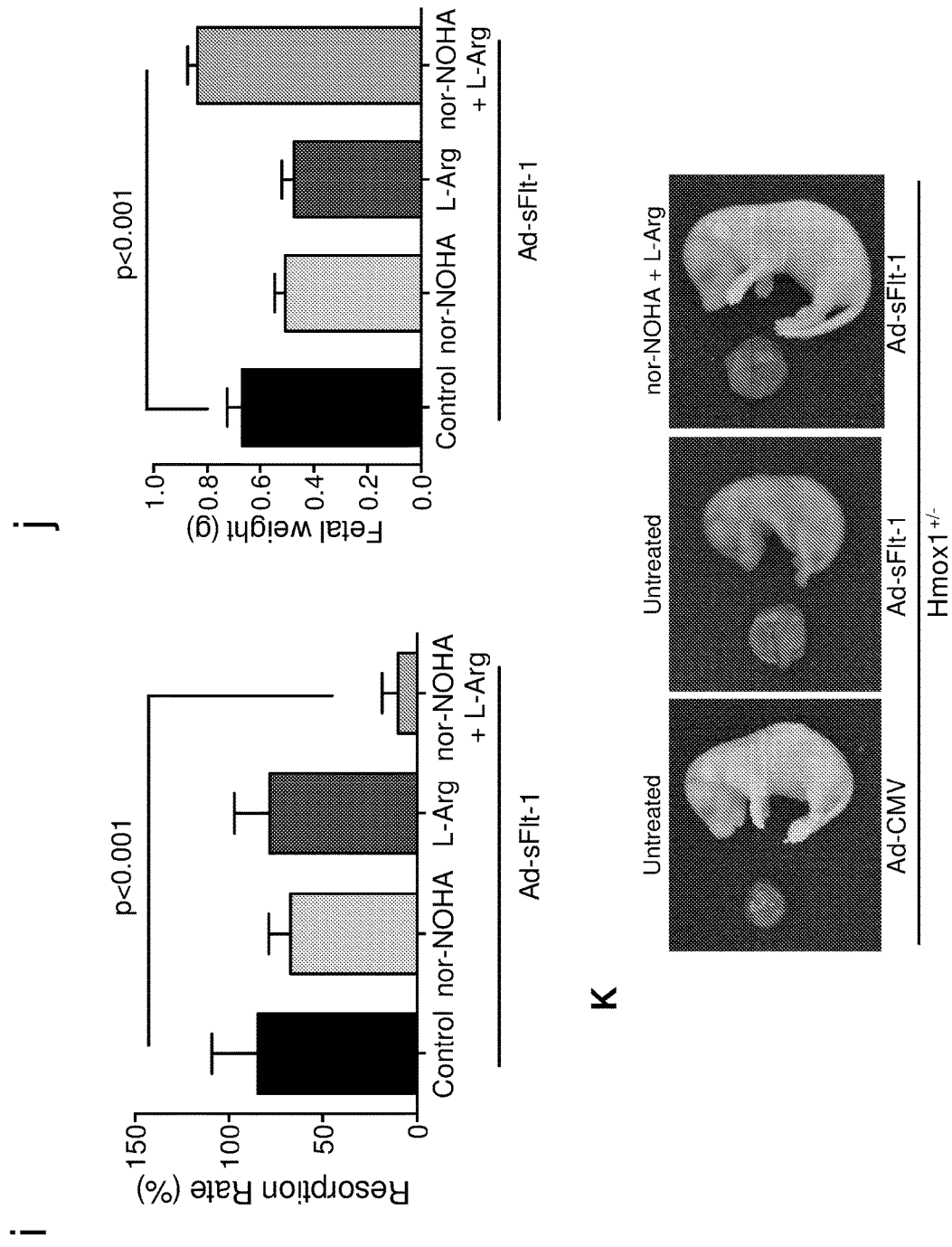

FIG. 5. Shift in arginine pathway rescues the preeclampsia phenotype in Hmox1$^{+/-}$ pregnant mice under high sFlt-1 environment. (A) Representative glomeruli from Ad-sFlt-1 injected Hmox1$^{-/-}$ mice treated with arginase inhibitor (nor-NOHA), L-arginine or arginase inhibitor and L-arginine. Serial sections were stained with Hematoxylin and Eosin (HE) and Periodic acid-Schiff (PAS). (B) 24 h urinary albumin excretion normalised to urinary creatinine and expressed as a urinary albumin:creatinine ratio from Ad-sFlt-1 injected Hmox1$^{-/-}$ mice treated with arginase inhibitor (nor-NOHA), L-arginine or arginase inhibitor and L-arginine. (C) Urinary Kidney Injury Molecule-1 (pg/ml) (KIM-1) from Ad-sFlt-1 injected Hmox1$^{-/-}$ mice treated with arginase inhibitor (nor-NOHA), L-arginine or arginase inhibitor and L-arginine. (D) Immunohistochemical localisation of 3-nitrotyrosine in kidney sections from Ad-sFlt-1 injected Hmox1$^{-/-}$ mice treated with arginase inhibitor and L-arginine or untreated controls. (E) Relative mRNA expression of arginase-1 in Hmox1$^{+/+}$ and Hmox1$^{-/-}$ placenta from Ad-sFlt-1 injected Hmox1$^{+/-}$ pregnant mice. (F) Mean arterial blood pressure (MAP) recorded at day 18 of gestation in timed pregnant Ad-sFlt-1 injected Hmox1$^{+/-}$ mice treated with arginase inhibitor, L-arginine or and L-arginine and arginase inhibitor or untreated controls. (G) 24 h urinary albumin:creatinine ratio at day 18 of gestation in timed pregnant Ad-sFlt-1 injected Hmox1$^{+/-}$ mice treated with arginase inhibitor, L-arginine or and L-arginine and arginase inhibitor or untreated controls. (H) Urinary Kidney Injury Molecule-1 (pg/ml) (KIM-1) at day 18 of gestation in timed pregnant Ad-sFlt-1 injected Hmox1$^{+/-}$ mice treated with arginase inhibitor, L-arginine or and L-arginine and arginase inhibitor or untreated controls. (I) Total fetal resorption rate expressed as percentage at day 18 of gestation in timed pregnant Ad-sFlt-1 injected Hmox1$^{+/-}$ mice treated with arginase inhibitor, L-arginine or and L-arginine and arginase inhibitor or untreated controls. (J) Average fetal weight expressed as grams per pup at day 18 of gestation in timed pregnant Ad-sFlt-1 injected Hmox1$^{+/-}$ mice treated with arginase inhibitor, L-arginine or and L-arginine and arginase inhibitor or untreated controls. (K) Representative pups and placentas at day 18 of gestation in timed pregnant Ad-sFlt-1 injected Hmox1$^{+/-}$ mice treated with arginase inhibitor and L-arginine or untreated controls. Results are representative or expressed as mean (±SEM) and analysed by 1-way repeated-measures ANOVA followed by Student-Newman-Keuls post hoc tests.

Figure 6:
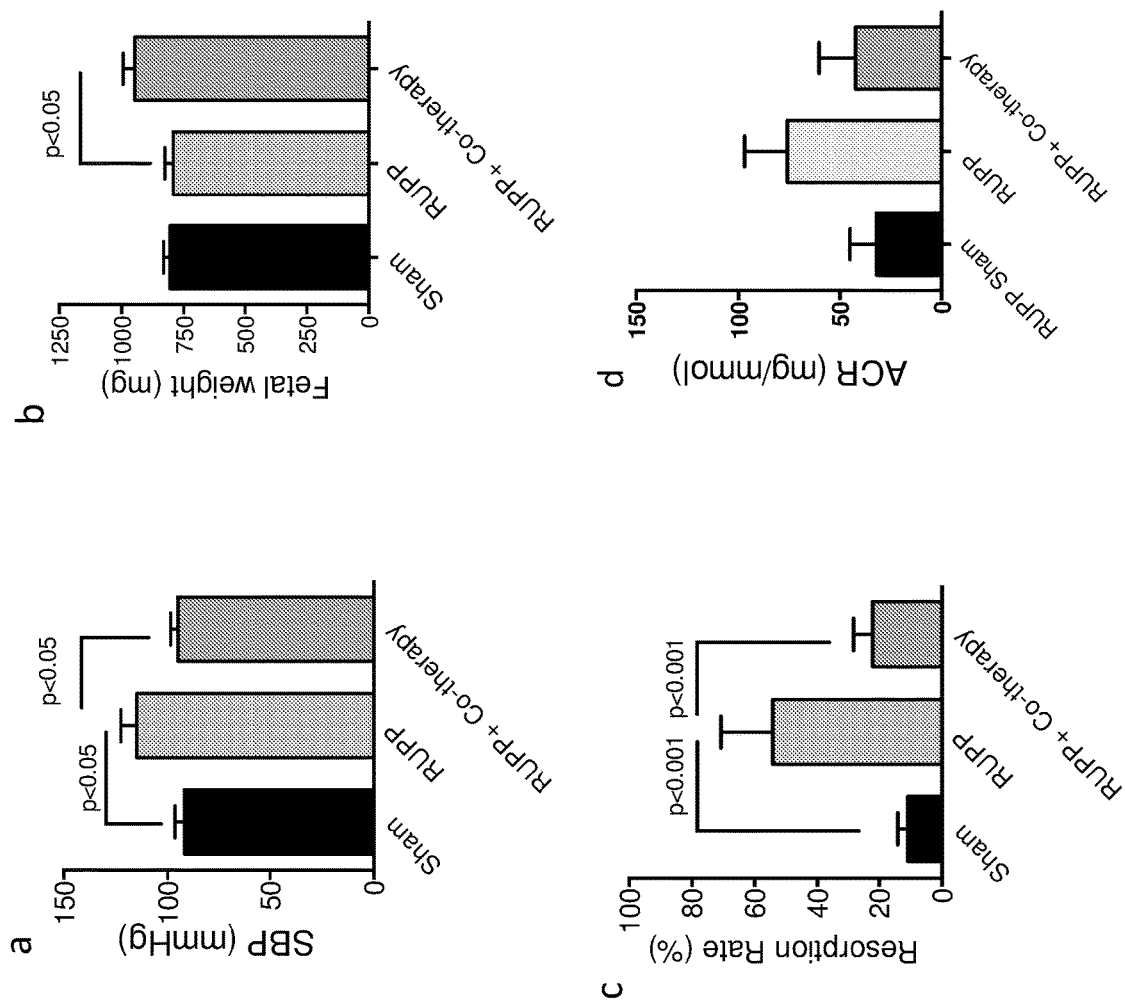
Figure 6:
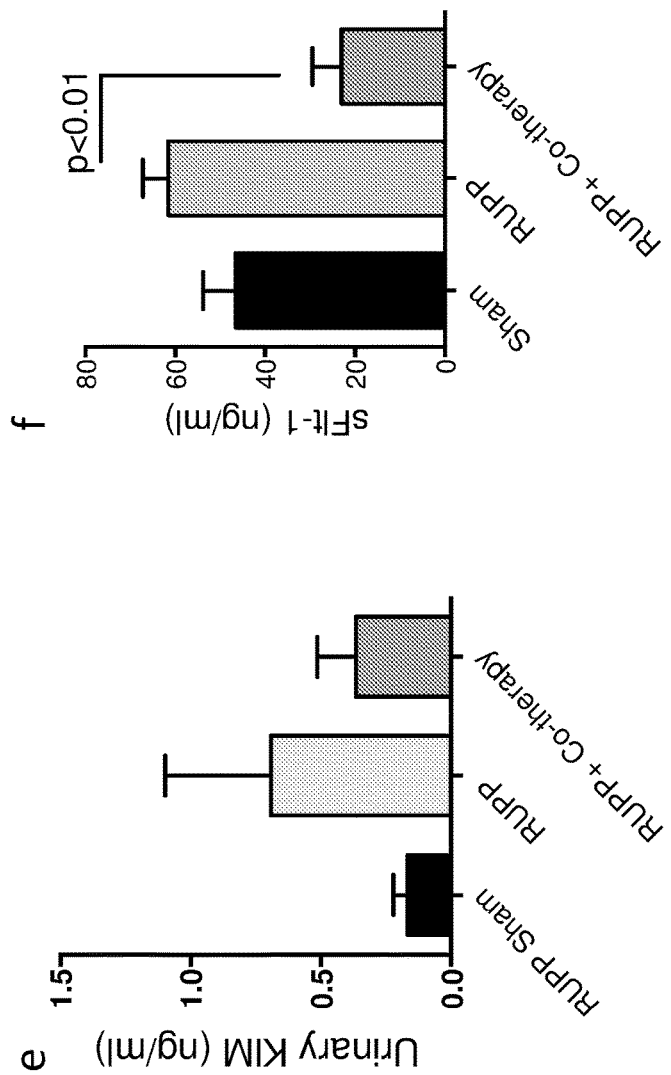

FIG. 6. The effect of L-Arg and arginase inhibitor combined treatment in RUPP model of preeclampsia. (A) Systolic arterial blood pressure (SBP). (B) Average fetal weight expressed as grams per pup at day 18. (C) Total fetal resorption rate expressed as percentage at day 18 of gestation from timed pregnant C57/bI6 mice undergone RUPP or Sham surgery and treated with or without L-arginine and arginase inhibitor. (D) Urinary albumin:creatinine ratio at day 18 of gestation in timed pregnant mice undergone RUPP or Sham surgery and treated with or without L-arginine and arginase inhibitor. (E) Urinary Kidney Injury Molecule-1

(pg/ml) (KIM-1) at day 18 of gestation from timed pregnant C57/bl6 mice undergone RUPP or Sham surgery and treated with or without L-arginine and arginase inhibitor. (F) Circulating sFlt-1 levels in at day 18 of gestation from timed pregnant C57/bl6 mice undergone RUPP or Sham surgery and treated with or without L-arginine and arginase inhibitor.

Figure 7:
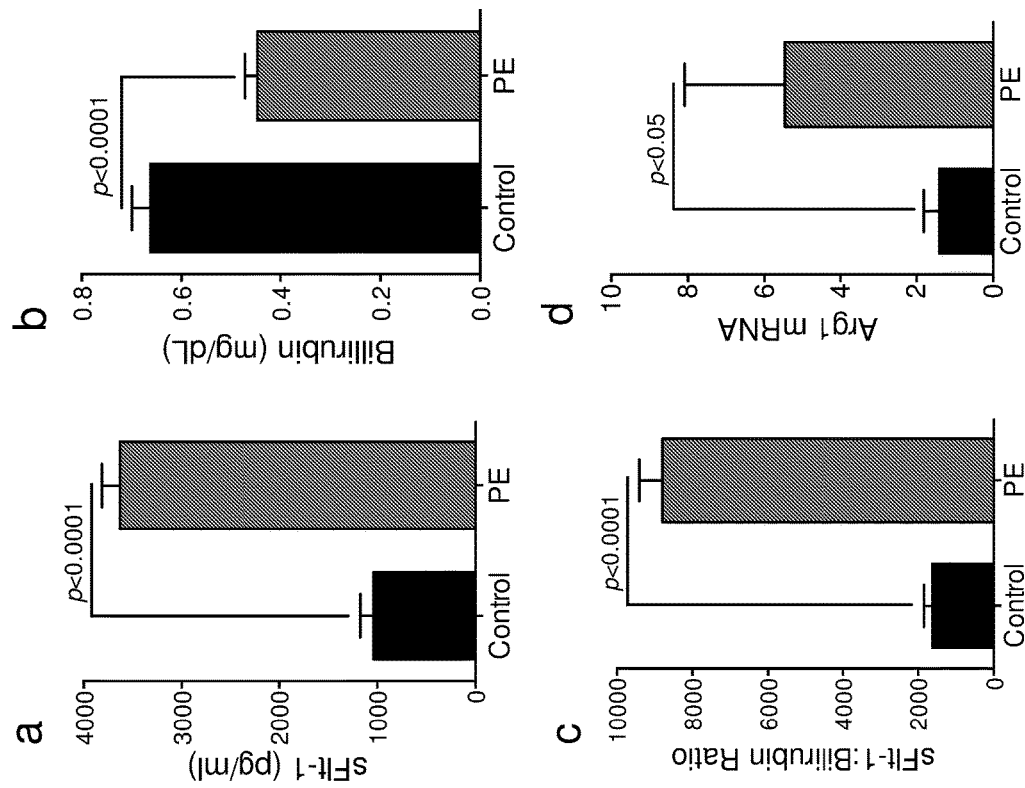
Figure 7:
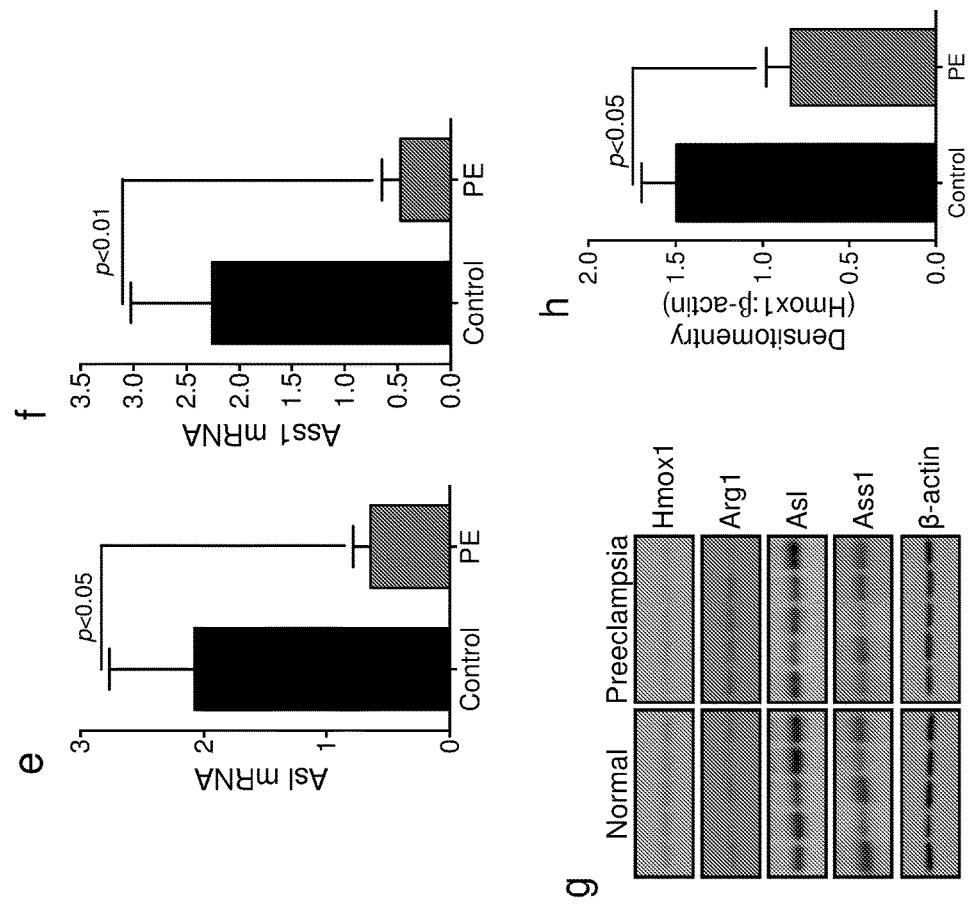
Figure 7:
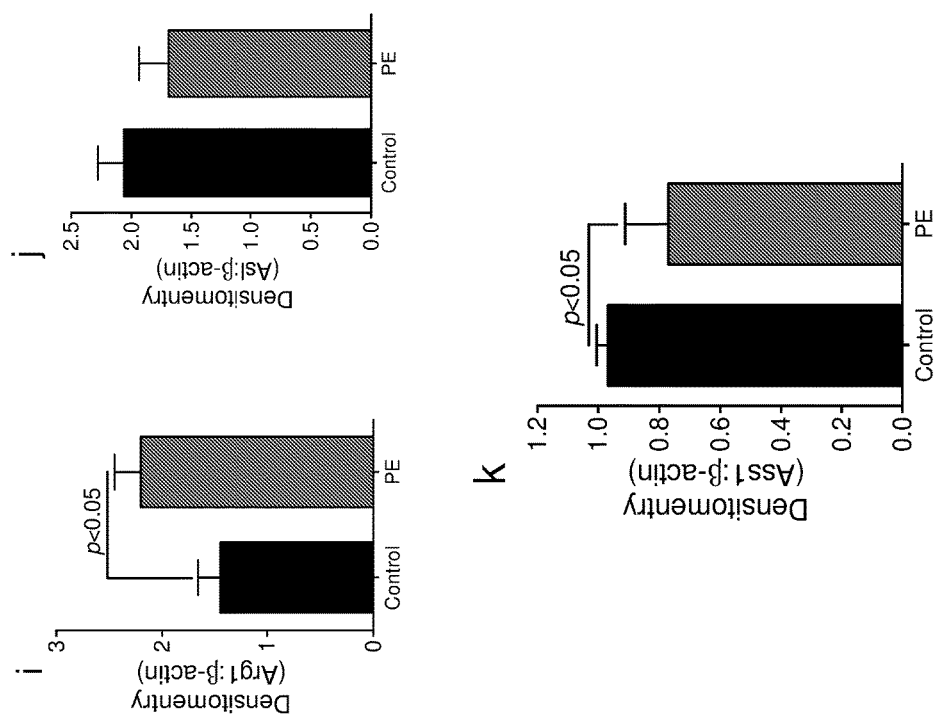
Figure 7:
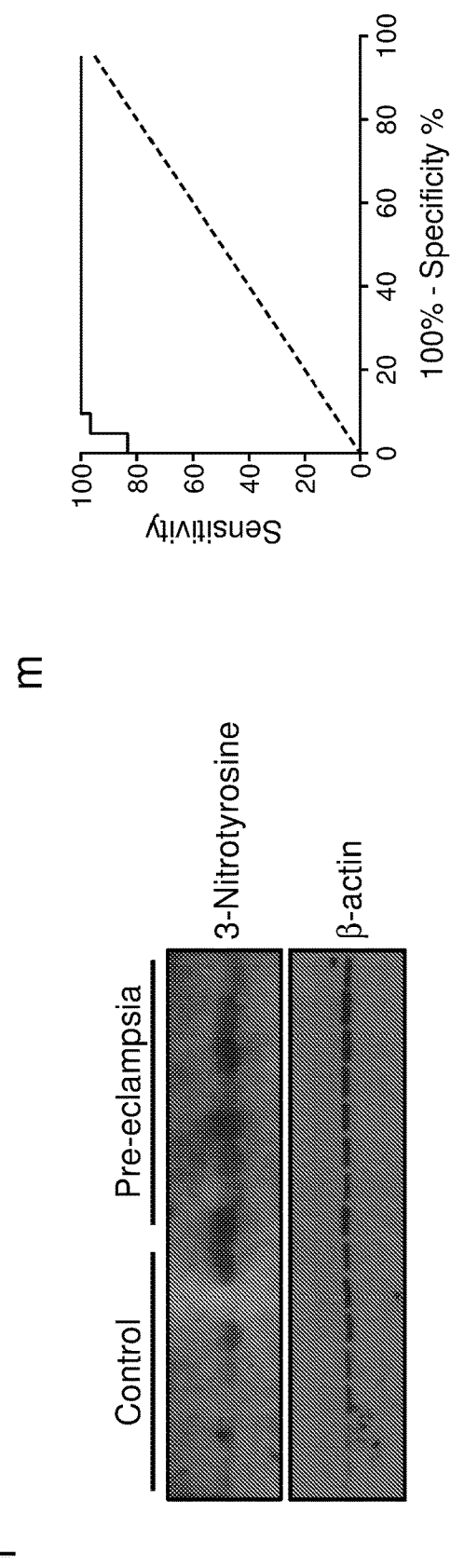
Figure 8:
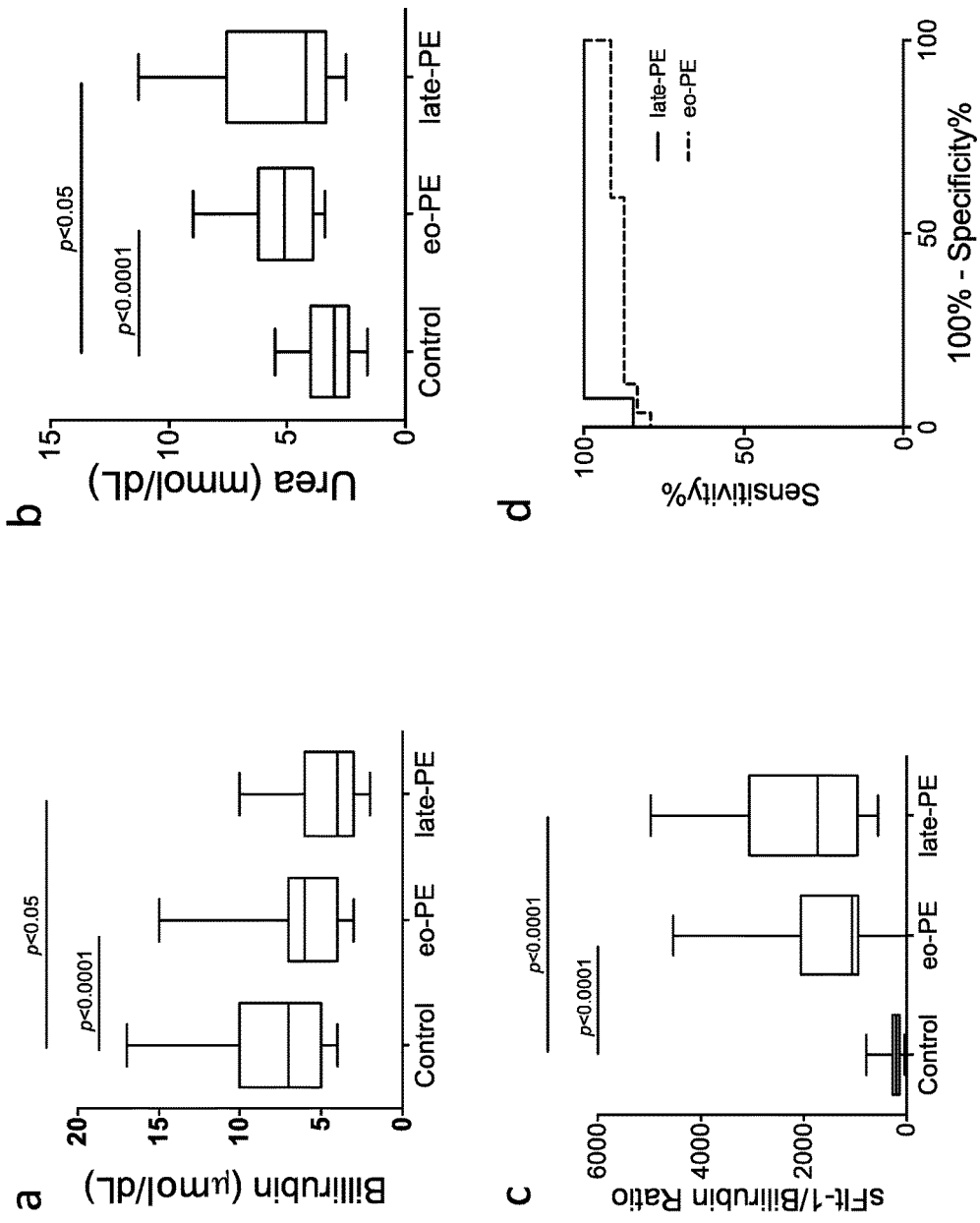
Figure 8:
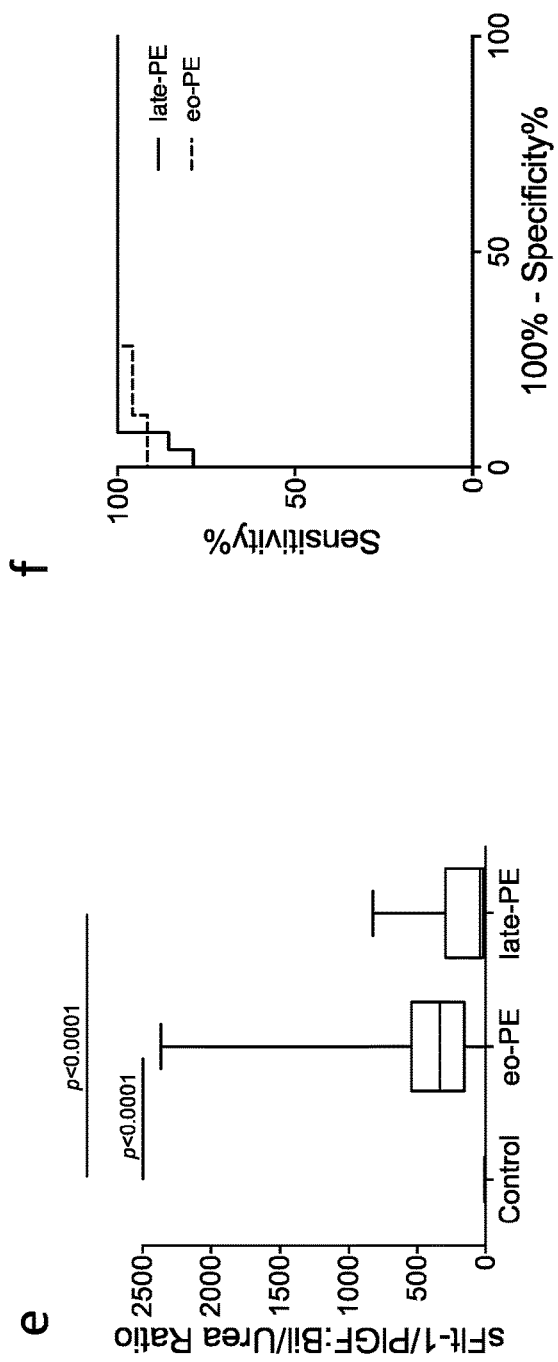

FIG. 7. Preeclampsia patients with elevated sFlt-1 levels have an altered arginine biosynthetic pathway. (A) Plasma sFlt-1 levels in early onset preeclamptic pregnancies and gestationally age-matched control group. (B) Plasma bilirubin levels in early onset preeclamptic pregnancies and gestationally age-matched control group. (C) Levels of sFlt-1:bilirubin expressed as a ratio in in early onset preeclamptic pregnancies and gestationally age-matched control group. (D-F) Relative mRNA expression of arginase 1, argininosuccinate lyase (Asl) and argininosuccinate synthase-1 (Ass1) in a subset of early onset preeclamptic placenta with significantly elevated levels of sFlt1 when compared to gestationally age-matched control group. (G-K) Western blot and densitometric analysis of arginase 1, Asl and Ass1 in placenta from normal pregnancies and pregnancies complicated with preeclampsia. β-actin served as loading control and all densitometric analysis were normalized to β-actin. (L) Western blot analysis showing 3-Nitrotyrosine expressions in placental lysates of normal and preeclamptic women. (M) ROC curve for prediction of adverse outcomes using the sFlt-1:Bilirubin ratio FIG. 8. Ratios between sFlt-1 and Bilirubin or sFlt-1: PlGF to Bilrulin:Urea for women destined to develop preeclampsia. (A) Plasma bilirubin (μmol/dL) levels in pregnancies complicated with early-onset, late-onset preeclampsia and compared to age matched normal pregnancies. (B) Plasma urea (mmol/dL) levels in pregnancies complicated with early-onset, late-onset preeclampsia and compared to age matched normal pregnancies. (C) Soluble Flt1:bilirubin ratio in pregnancies complicated with early-onset preeclampsia and compared to age matched normal pregnancies. (D) ROC curve for prediction of adverse outcomes using the sFlt-1:bilirubin ratio. (E) sFlt1:PlGF:bilirubin:urea ratio in pregnancies complicated with early-onset, late-onset preeclampsia and compared to age matched normal pregnancies. (F) ROC curve for prediction of adverse outcomes using the sFlt-1:PlGF:bilirubin:urea ratio.

Figure 9:
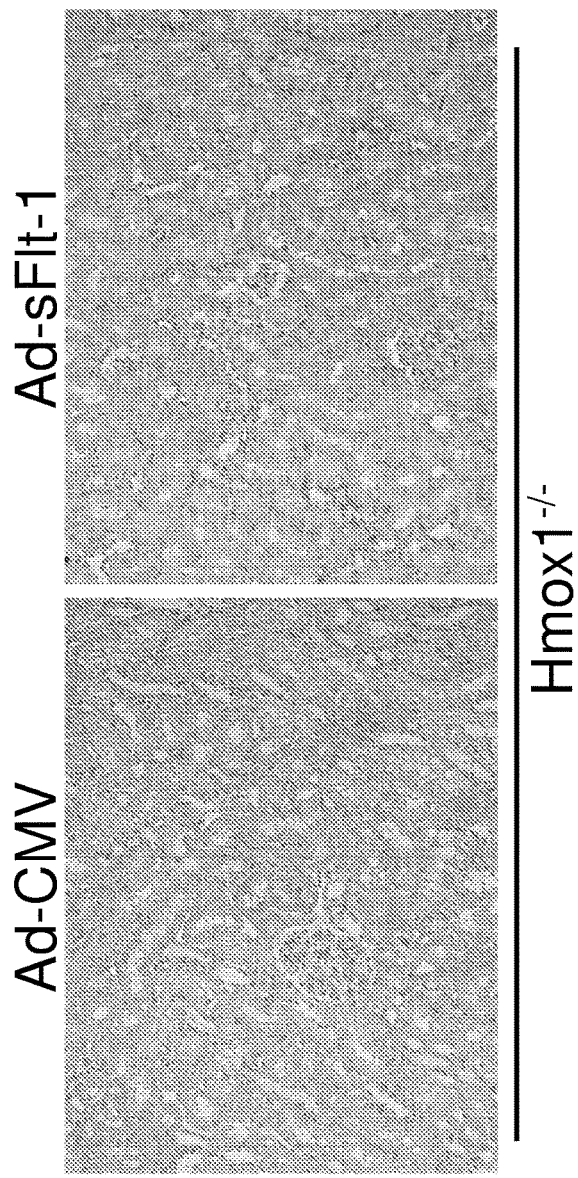

FIG. 9. Perl's Prussian blue stain demonstrating iron deposition in sFlt-1 treated Hmox1−/− mice.

FIG. 10. Proposed schematic pathway to explain a tailored therapeutic approach to preeclampsia

MATERIALS AND METHODS

Patients' Sample

Predictive study: This was a prospective study, which took place at St George's Hospital University of London between September 2012 and December 2014. Written informed consent was obtained from all women agreeing to participate in the study. The study was approved by the London-Stanmore Research Ethics Committee. The inclusion criteria for this study were women with a singleton pregnancy presenting after 20+0 weeks of gestation with symptoms or signs of suspected preeclampsia. Assay operators were blinded to the clinical information of the participants. Maternal blood was collected by venipuncture without anticoagulant. Samples were centrifuged with 2000×g and serum was pipetted and stored at −80° C. until testing. sFlt-1 and PlGF concentrations were determined in parallel and then measured by commercially available assays on Elecsys platform from Roche Diagnostics, Penzberg, Germany. The maternal serum bilirubin levels were measured using colorimetric Assay Kit.

Validation study: The Institutional Ethics Committee approved the blood and tissue collection, and written informed consent was obtained. Blood samples from women with singleton pregnancies recruited in low- and high-risk clinics and labor and delivery units. All women were followed up prospectively from enrollment until delivery. Maternal blood was collected by venipuncture without anticoagulant. Samples were centrifuged with 2000×g and serum was pipetted and stored at −80° C. until testing. sFlt-1 and PlGF concentrations were determined in parallel and then measured by commercially available ELISA assay kits. (R&D system). The maternal serum bilirubin levels were measured using colorimetric Assay Kit.

Experimental Animals

Non-pregnant studies were carried out twelve-week-old Hmox1$^{-/-}$ mice and Hmox1$^{+/+}$ mice. Animals were injected with 1×10$^9$ PFU of Ad-sFlt-1 or Ad-CMV (control) adenovirus by injection into the tail vein. Nine days after adenovirus administration, mice were individually placed in metabolic cages for 24 hours. Body weight, food and water intake, and urine volume were measured. Following urine measurements, blood sampling was undertaken on day 10, the animals were euthanized, and their kidneys and livers were collected for further analysis. Co-treatment rescue studies using arginase inhibitor and/or L-arginine supplementation were also undertaken in non-pregnant Hmox1$^{-/-}$ mice and Hmox1$^{+/+}$ animals. Mice were injected intraperitoneally with nor-NOHA (Bachem, Bubendorf, Switzerland) daily. L-arginine (Sigma-Aldrich, St. Louis, Mo.) was given to the animals by supplementing the drinking water with 25 g/L one week before the Ad-sFlt-1 adenovirus injection and until the end of the study.

Pregnant mice studies were carried out ten to twelve-week-old Hmox1$^{+/-}$ mice and Hmox1$^{+/+}$ mice or wild-type C57/Bl6 mice. The first day of pregnancy (E0.5) was defined by the presence of a vaginal plug the following morning. On E10.5 (second trimester) pregnant mice were injected with 1×10$^9$ PFU of Ad-sFlt-1 or Ad-CMV (control) adenovirus by injection into the tail vein. For RUPP study, on day 13 of gestation, time pregnant C57/Bl6 mice were anesthetized. An incision was made down the midline of the body and the abdominal aorta was isolated. The vessel was then restricted with 7.0 suture tied around a blunt needle (approximate diameter of 1 mm$^2$) placed on the aorta. The needle was then removed. Right ovarian artery was restricted with 7.0 suture. The incisions were closed and the mice were allowed to recover for five days. For the low-dose sFlt-1 experiment, 1×10$^8$ PFU of adenovirus expressing sFlt-1 was used. On E17.5 mice were individually placed in metabolic cages for 24 hours and arterial blood pressure was measured at E18.5 as described previously (Wang et al. 2013). In brief, mice were anesthetized by using a ketamine/xylazine cocktail, and the carotid artery was isolated and cannulated with a Millar 1-French Mikro-Tip pressure catheter connected to a pressure transducer (ADInstruments Ltd, Oxford, UK). After 30 minutes of blood pressure stabilization, arterial pressure was recorded and averaged over an additional 10-minute period. Following measurements, blood sampling was undertaken, the animals were euthanized, and their kidneys, livers, and placentas were collected. The live fetuses and placentas were counted and weighed. All experimentation was conducted in accordance with the United Kingdom Animals (Scientific Procedures) Act, 1986 with the use of procedures approved by the University Ethical Review Committee.

Biochemical Measurements in Blood and Urine

Urinary albumin was determined using Albuwell-M kits (Exocell Inc, Philadelphia, Pa.). Enzyme-linked immunosorbent assay kits for human and murine sFlt-1, KIM-1, and PlGF were obtained from R&D Systems and performed according to the manufacturer's specifications.

Real-Time Polymerase Chain Reaction

Sample preparation and real-time quantitative polymerase chain reaction was performed as described previously (Wang et al. 2013). monoclonal anti-3-Nitrotyrosine (1:1000 dilution, Abcam), anti-argininosuccinate synthase (1:500), Abcam), anti-argininosuccinate lyase (1:500, Abcam), anti-arginase-1 antibody (1:500, Genetex) and anti-beta actin (1:10000, Sigma).

Immunohistochemistry

Human and murine placental tissues were prepared for immunohistochemistry as previously described. Immunohistochemistry was performed by using antibodies to Arginase-1, Ass1, Asl, and 3-nitrotyrosine. The following antibodies were used: (1) anti-arginase-1 antibody (1:50, Genetex); (2) anti-argininosuccinate synthase (1:100), Abcam); (3) anti-argininosuccinate lyase (1:100, Abcam) and (4) anti-3-Nitrotyrosine (1:100 dilution, Abcam). Sections from mouse kidneys or human placental biopsies were rehydrated, blocked with the use of normal serum, and incubated with primary antibody for 2 hours at room temperature. Visualization was performed by using a Vectastain ABC kit, with DAB. Slides were counterstained with hematoxylin. The staining was analysed by using a Nikon inverted microscope and Image Pro-Plus image analysis software.

Gene Array

RNA samples were prepared from mouse kidney tissues as described above and submitted to ARK-Genomics, University of Edinburgh where they underwent quality analysis Western Blot Analysis Kidney lysates were dissected, and samples were snap-frozen in liquid nitrogen. Western blots were performed with monoclonal anti-3-Nitrotyrosine (1:1000 dilution, Abcam), anti-argininosuccinate synthase (1:500), Abcam), anti-argininosuccinate lyase (1:500, Abcam), anti-arginase-1 antibody (1:500, Genetex) and anti-beta actin (1:10000, Sigma). An anti-rabbit or anti-mouse IgG secondary antibody conjugated with horseradish peroxidase (1:1000 dilution, Transduction Laboratories) was used.

Statistical Analysis Results are presented as means ±SEM, and comparisons between multiple groups were made using ANOVA. Significant differences are reported when $P<0.05$.

RESULTS

To test the concept that severe preeclampsia may arise due to partial loss of VEGF and Hmox1 activity and to accurately reflect the human PE-like conditions, we delivered sFlt-1 systemically to haploinsufficient (carrying a single Hmox1 allele) Hmox1 ($Hmox1^{+/-}$) pregnant mice by intravenous injection of adenovirus encoding sFlt-1 (Ad-sFlt-1) at two doses. Using this approach, we reproduced the significantly increased sFlt-1 in the blood plasma of pregnant mice. As one of the diagnostic criteria for preeclampsia is hypertension, mean arterial blood (MAP) pressure was measured at day 18.5 gestation (FIG. 3a) or systolic blood pressure (SBP) continuously using implanted radio-telemeters. Both modes of measurement showed severely elevated blood pressure at E18.5 in Ad-sFlt-1 treated $Hmox1^{+/-}$ group compared with their wild-type littermates at the higher circulating level of sFlt-1. Moreover, radio-telemetry studies showed a continuous rapid increase in SBP that reached a maximum at E18.5 in sFlt-1 treated $Hmox1^{+/-}$ mice. Glomerular endotheliosis is a major feature of severe preeclampsia and a good indicator of widespread maternal endothelial damage Renal histological analysis from these mice revealed lobulation and scarring glomeruli typical of severe glomerular endotheliosis (FIG. 3b). Consistent with the renal damage, urinary albumin excretion was also significantly increased in these animals compared to the wild-type mice (FIG. 3c). Severe renal injury was further substantiated by the increase in urinary levels of Kidney Injury Molecule-1 (a specific marker for proximal tubule injury associated with severe preeclampsia) (FIG. 3d) and elevated urinary sFlt-1 levels (associated with severe preeclampsia) (FIG. 3e).

Abnormal liver function tests are reported to be associated with an increased risk for adverse maternal outcomes and both alanine aminotransferase (ALT) and aspartate aminotransferase (AST), markers of acute liver injury, were significantly increased in Hmox1 compromised mice under the high sFlt-1 challenge (FIG. 3f and g). In addition, soluble Endoglin (sEng), a marker of endothelial activation and reported to induce severe preeclampsia in concert with sFlt-1 was also increased (FIG. 3h). Consistent with the preeclampsia phenotype, reduced fetal weight (FIG. 3i) and increased fetal resorption (FIG. 3j) was found in $Hmox1^{+/-}$ mice. Representative images of pups harvested from sFlt-1 treated $Hmox1^{+/-}$ mice produced smaller and poorly vascularised embryos. Placental Arg1 levels in $Hmox1^{+/+}$ and $Hmox1^{+/-}$ placenta harvested from Ad-sFlt-1 treated $Hmox1^{+/-}$ mice showed significantly elevated Arg1 mRNA in $Hmox1^{+/-}$ placenta (FIG. 4k). We measured plasma bilirubin, as it is a recognized marker of Hmox1 activity and noted that sFlt-1 induced a dramatic increase in plasma bilirubin in the wild-type pregnancies, but the increase was blunted in Hmox1 compromised animals (FIG. 3l). Placental Hmox activity studies in sFlt-1 treated $Hmox1^{+/+}$ and $Hmox1^{+/-}$ mice mirrored the plasma bilirubin results to further confirm the validity of using bilirubin as a substitute marker of Hmox activity. This raised the possibility that high sFlt-1 induces Hmox1 activity as a stress response mechanism in normal pregnancy, but this mechanism is impaired when Hmox1 activity is limited. These studies show that high sFlt-1 and low Hmox1 activity produce a severe form of the preeclampsia phenotype, which could now be used as a surrogate marker to support a tailored therapy development.

To test the notion directly that elevated sFlt-1 and Hmox1 deficient environment may induce severe preeclampsia, we delivered sFlt-1 systemically to $Hmox1^{-/-}$ mice. Intravenous injection of adenovirus encoding sFlt-1 (Ad-sFlt-1) produced high levels of sFlt-1 in the circulation and in the urine, suggesting renal damage. As Hmox1 deficiency also renders the mouse infertile, these experiments have been conducted in the non-pregnant state and focused on the subsequent renal damage. Complete loss of Hmox1 and high circulating sFlt-1 caused severe focal glomerular lesions characterized by glomerular endothelial swelling of varying extent with narrowing or occlusion of glomerular capillary loops, glomerulosclerosis, mesangiolysis, lobulation and scarring, with karyorrhexis in some cells (FIG. 4a). This was confirmed by randomized single-blind scoring of kidney sections which showed significantly higher levels of abnormal glomeruli in Hmox1$^{-/-}$ mice treated with sFlt-1 (FIG. 4b). Consistent with the severe renal damage, there was an increase in proteinuria (FIG. 4c). High sFlt-1 caused up-regulation in plasma bilirubin activity in wild-type mice, a surrogate marker of Hmox1 activity, but sFlt-1 did not increase Hmox1 activity (low plasma bilirubin levels) in the knockout animals (FIG. 4d). To investigate the mechanism responsible for sFlt-1-induced renal injury, we studied changes in kidney gene expression after mice were exposed to high levels of sFlt-1 for 10 days. Affymetrix genechip microarray analysis revealed several up-regulated (>20-fold) genes in kidneys of Hmox1$^{-/-}$ mice treated with sFlt-1. One of the most significantly up-regulated genes was arginase-1 (Arg1), which was confirmed by real-time PCR (FIG. 4e) and arginase activity assay (FIG. 4f). The substrate for Arg1 is L-arginine. L-arginine availability is also the major determinant of nitric oxide (NO) bioavailability, being the substrate for endothelial NO synthase (NOS). The rate-limiting step in L-arginine synthesis is the transformation of L-citrulline, a by-product of NO production, into arginino-succinate by argininosuccinate synthetase (Ass) and argininosuccinate lyase (Asl) to recycle argininosuccinate into L-arginine. Overexpression of sFlt-1 significantly inhibited mRNA expression of Asl (FIG. 4g) and Ass1 (FIG. 4h) in Hmox1$^{-/-}$ mice, suggesting that a decrease in Hmox1 activity in preeclampsia may lead to a major dysregulation of the arginine pathway enzymes. It is also known that the expression of the oxidative stress marker, nitrotyrosine, is greater in normal pregnancy than in preeclamptic placenta. The dysregulation in the arginine metabolism and lack of rise in bilirubin in response to sFlt-1 prompted us to investigate reactive nitrotyrosine species in these mice kidneys. Hmox1$^{-/-}$ mice treated with Ad-sFlt-1 revealed higher abundance of 3-nitrotyrosine, a marker for reactive nitrogen species, in kidney lysates using western blot analysis (FIG. 4i).

As overexpression of sFlt-1 in Hmox1$^{-/-}$ mice leads to an increase in Arg1 activity, we directly tested whether inhibition of arginase activity together with supplementation of L-arginine could rescue the severe renal injury seen in these mice. When arginase activity was inhibited by daily intra-peritoneal injection of N-ω-hydroxy-L-nor-arginine (nor-NOHA) and L-arginine was added ad libitum in drinking water, this rescued renal glomerulosclerosis and mesangi-olysis (FIG. 5a). It also significantly inhibited renal damage detected by proteinuria (FIG. 5b) and urinary KIM-1 levels (FIG. 5c) were markedly reduced in Hmox1$^{-/-}$ mice exposed to high sFlt-1. Renal 3-nitrotyrosine immunostain-ing also appeared diminished following co-therapy treatment in Hmox1$^{-/-}$ mice (FIG. 5d). Placental Arg1 levels in Hmox1$^{+/+}$ and Hmox1$^{+/-}$ placenta harvested from Ad-sFlt-1 treated Hmox1$^{+/-}$ mice showed significantly elevated Arg1 mRNA in Hmox1$^{+/-}$ placenta (FIG. 5e). L-Arginine supple-mentation ad libitum in the drinking water significantly reduced mean arterial blood pressure (MAP) in Ad-sFlt-1 treated Hmox1$^{+/-}$ mice (FIG. 5f) but showed no significant improvement in fetal resorption rate or average fetal weight (FIG. 5j). Whereas, daily nor-NOHA therapy reduced resorption rate (FIG. 5i) but had no significant effect on MAP (FIG. 5f) or fetal weight. Both therapies also showed no significant improvements in proteinuria (FIG. 5g). However, when arginase activity was inhibited by daily together with L-arginine supplementation, this lowered the blood pressure (FIG. 5f), improved fetal weight distribution to normal Ad-CMV range (FIG. 5j). The co-therapy produced healthy looking fetuses (FIG. 5k) and led to marked and significant reduction in fetal resorption rate (FIG. 5i). Co-therapy also significantly inhibited renal damage detected by proteinuria (FIG. 5g) and urinary KIM-1 levels (FIG. 5h) were markedly reduced in Hmox1$^{+/-}$ mice exposed to high sFlt-1.

Reduced uteroplacental perfusion and the resulting pla-cental ischemia is another major hallmark of preeclampsia. More recently, Gilbert et al showed that placental ischemia produced by the reduced uterine placental perfusion (RUPP) model in the rat increased sFlt-1 and sEng and significantly decreased Hmox1 expression. We have miniaturised and adapted the rat RUPP model to the mouse to test our novel nor-NOHA and L-Arginine co-therapy. As previously reported with the rat RUPP, RUPP surgery in wild-type C57BL/6 mouse significantly increased systolic blood pres-sure (SBP) (FIG. 6a) and sFlt-1 levels (FIG. 6f) compared to Sham controls. Similarly, proteinuria (FIG. 6d) and resorp-tion rate (FIG. 6c) were also increased following RUPP intervention. However, co-therapy with nor-NOHA and L-Arginine was able to reduce systolic blood pressure (SBP) (FIG. 6a), sFlt-1 (FIG. 6f), proteinuria (FIG. 6d) and resorp-tion rate (FIG. 6c) and normalised fetal weight (FIG. 6b) in RUPP mice.

To test the idea that severe preeclampsia arises in a selected group of pregnant women for whom Hmox1 activity and VEGF signalling is defective, we measured plasma sFlt-1 in women with severe preeclampsia and controls. As expected, plasma sFlt-1 was significantly increased (FIG. 7a) and in these individuals with high sFlt-1, plasma bili-rubin was found to be low (FIG. 7b). Furthermore, the ratio of sFlt-1 to bilirubin was significantly higher in PE samples (FIG. 7c). We next compared the expression of the enzymes involved in arginine metabolism in placenta obtained from normal pregnancies and pregnancies complicated by preec-lampsia to see if these were altered in a similar manner to that observed in the high sFlt-1 and low Hmox1 environ-ment of our mouse model of preeclampsia. Placental Arg1 was dramatically increased at both mRNA (FIG. 7d) and protein levels (FIGS. 7g and i), consistent with plasma arginase levels being increased in preeclampsia. In contrast, transcript and protein levels of Asl (FIG. 7e, 7g, 7j) and Ass1 (FIG. 7f, 7g, 7k) were significantly decreased. Western blot analysis revealed increased 3-nitrotyrosine expressions in placental lysates from women with preeclampsia (FIG. 7l). Receiver-operating characteristics (ROC) analysis showed that the sFlt-1/bilirubin ratio had good discriminative power between women who developed early severe preeclampsia and those who did not develop the disorder, with an area under the ROC curve of 0.98 (FIG. 7m)

To test whether dysregulation in angiogenic imbalance, combined with a decrease in Hmox1 activity and an increased arginase activity could be used as a potential diagnostic tool, plasma levels of sFlt-1, PlGF, bilirubin and urea were measured at mid-gestation in women with signs of suspected preeclampsia. Analysis showed plasma bilirubin to be significantly decreased and urea to be significantly increased in patients who developed early and late onset preeclampsia at mid-gestation (FIGS. 8a and b). sFlt-1 to bilirubin ratio also showed a significant increase in both early and late onset preeclampsia (FIG. 8c) with an area under the ROC curve of 0.865 and 0.989 respectively (FIG. 8d). However, when assessed as a combination of four parameters and expressed as a ratio of [sFlt1:PlGF]/[Biliru-bin:Urea], our novel diagnostic algorithm showed a signifi-cant increase in [sFlt1:PlGF]/[Bilirubin:Urea] ratio in early and late onset preeclampsia group when compared to normal pregnancies (FIG. 8e). Furthermore, receiver-operating characteristics (ROC) analysis showed that this ratio had good discriminative power between women who developed early severe preeclampsia and late onset preeclampsia when compared to those who did not develop the disorder, with an area under the ROC curve of 0.983 and 0.985 respectively (FIG. 8f).

The invention claimed is:

1. A method of treating preeclampsia in a subject, the method comprising administering to the subject (a) a therapeutically effective amount of L-arginine or a salt thereof, or citrulline or a salt thereof, or a precursor of L-arginine or a salt thereof, or a combination of any of the foregoing; and (b) an inhibitor of arginase; and optionally (c) an iron chelating agent.

2. The method of claim 1 wherein the inhibitor of arginase is nor-NOHA or a salt thereof.

3. The method of claim 1 wherein the L-arginine or a salt thereof, or citrulline or a salt thereof, or precursor of L-arginine or a salt thereof, or combination of any of the foregoing are administered orally.

4. The method of claim 1 wherein the inhibitor of arginase is administered intramuscularly or intraperitoneally.

5. The method of claim 1 wherein the subject has a high ratio of sFlt-1 compared to a heme breakdown product.

6. The method of claim 1 comprising administering a therapeutically effective amount of (a) L-arginine or a salt thereof, or citrulline or a salt thereof, or a combination of any of the foregoing; and (b) an inhibitor of arginase to the subject.

7. The method of claim 1 comprising administering to the subject (a) a therapeutically effective amount of L-arginine or a salt thereof, or citrulline or a salt thereof, or a precursor of L-arginine or a salt thereof, or a combination of any of the foregoing; and (b) an inhibitor of arginase; and (c) an iron chelating agent.

8. The method of claim 7 wherein the iron chelating agent is deferoxamine.

* * * * *